United States Patent
Lee et al.

(10) Patent No.: US 11,955,810 B2
(45) Date of Patent: Apr. 9, 2024

(54) WIRELESS POWER RECEPTION AND OBJECT STIMULATION APPARATUS

(71) Applicant: Samsung Electronics Co., Ltd., Suwon-si (KR)

(72) Inventors: Jaechun Lee, Seoul (KR); Young Jun Hong, Seoul (KR); Sang Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 280 days.

(21) Appl. No.: 17/117,446

(22) Filed: Dec. 10, 2020

(65) Prior Publication Data

US 2021/0320527 A1 Oct. 14, 2021

(30) Foreign Application Priority Data

Apr. 14, 2020 (KR) .................. 10-2020-0045121

(51) Int. Cl.
*H02J 50/12* (2016.01)
*A61N 1/372* (2006.01)
*A61N 1/378* (2006.01)
*H04B 5/00* (2006.01)

(52) U.S. Cl.
CPC .......... *H02J 50/12* (2016.02); *A61N 1/37229* (2013.01); *A61N 1/3787* (2013.01); *H04B 5/0037* (2013.01); *H04B 5/0081* (2013.01)

(58) Field of Classification Search
CPC ...... H02J 50/12; H02J 2310/23; H02J 50/402; H02J 50/27; A61N 1/37229; A61N 1/3787; A61N 1/0534; A61N 1/0541; A61N 1/36038; A61N 1/3605; A61N 1/3956; A61N 1/3975; H04B 5/0037;
(Continued)

(56) References Cited

U.S. PATENT DOCUMENTS 2,415,808 A * 2/1947 Buckley ................. G01V 3/087
324/67
5,923,544 A * 7/1999 Urano ................. H02M 3/3382
320/108
(Continued)

FOREIGN PATENT DOCUMENTS

CN 100571364 C 12/2009
JP 2011-72452 A 4/2011
(Continued)

*Primary Examiner* — Daniel Cavallari
*Assistant Examiner* — Brian K Baxter
(74) *Attorney, Agent, or Firm* — NSIP Law

(57) ABSTRACT

A wireless power reception apparatus includes: a first electrode including a coil shape; a second electrode including the coil shape; an electrode capacitor connected between the first electrode and the second electrode; an electrode signal transceiver connected to the first electrode and the second electrode; a power receiver connected to the first electrode and the second electrode, separately from the electrode signal transceiver; a resonant capacitor; and first capacitor and a second capacitor configured to connect a conducting line between the first electrode and the power receiver and a conducting line between the second electrode and the power receiver, wherein the first electrode and the second electrode are wound in the same direction.

24 Claims, 22 Drawing Sheets

(58) Field of Classification Search
CPC ............ H04B 5/0081; A61M 5/14276; A61M 2205/8243; H01F 27/28; H01F 2005/006; H01F 2038/146
See application file for complete search history.

(56) References Cited

U.S. PATENT DOCUMENTS

| | | | |
|---|---|---|---|
| 8,008,102 B2* | 8/2011 | Vinciguerra | B82Y 20/00 977/750 |
| 9,962,113 B2 | 5/2018 | Lang et al. | |
| 10,022,545 B1* | 7/2018 | Giuffrida | A61N 1/36003 |
| 10,119,837 B2* | 11/2018 | Gliner | A61B 34/20 |
| 11,006,998 B2* | 5/2021 | Tang | A61N 1/37252 607/60 |
| 2006/0064143 A1* | 3/2006 | Von Arx | A61N 1/37252 607/60 |
| 2006/0085041 A1* | 4/2006 | Hastings | A61N 1/37223 607/33 |
| 2007/0150038 A1* | 6/2007 | Hastings | A61N 1/37223 607/119 |
| 2008/0158432 A1* | 7/2008 | Hwang | H01Q 1/44 348/725 |
| 2010/0191311 A1* | 7/2010 | Scheiner | A61B 5/4047 607/66 |
| 2010/0211172 A1* | 8/2010 | Bellamkonda | A61B 5/0031 607/116 |
| 2010/0312164 A1* | 12/2010 | Forsell | B01D 46/68 604/9 |
| 2011/0144619 A1* | 6/2011 | Meng | A61M 5/16881 604/141 |
| 2011/0248673 A1* | 10/2011 | Aerts | H02J 7/0044 320/108 |
| 2011/0306878 A1* | 12/2011 | Desimone | A61N 1/0536 600/431 |
| 2012/0253340 A1* | 10/2012 | Stevenson | H03H 7/0123 607/116 |
| 2013/0030271 A1* | 1/2013 | Lang | A61B 5/14532 600/347 |
| 2013/0289683 A1* | 10/2013 | Parker | A61N 1/3752 607/116 |
| 2014/0194949 A1* | 7/2014 | Wichner | A61N 1/323 607/48 |
| 2014/0213184 A1* | 7/2014 | Matsubara | H04B 5/0031 455/41.1 |
| 2015/0057653 A1* | 2/2015 | Sugiyama | H01F 27/2823 606/34 |
| 2015/0057720 A1* | 2/2015 | Ko | A61N 1/3756 607/60 |
| 2015/0072617 A1* | 3/2015 | Nowottnick | H04B 5/0031 455/41.2 |
| 2015/0244178 A1* | 8/2015 | Tang | H02J 50/10 307/104 |
| 2015/0365139 A1* | 12/2015 | Moon | H04B 5/02 455/41.1 |
| 2016/0157769 A1* | 6/2016 | Min | A61B 5/0536 600/547 |
| 2016/0164332 A1* | 6/2016 | Elkhouly | H02J 50/12 320/108 |
| 2017/0353061 A1* | 12/2017 | Maniktala | H02J 50/005 |
| 2018/0048055 A1* | 2/2018 | O'Driscoll | H01Q 7/00 |
| 2018/0207429 A1* | 7/2018 | Reinke | A61B 5/6867 |
| 2018/0280694 A1* | 10/2018 | Mashiach | A61N 1/3756 |
| 2018/0301805 A1* | 10/2018 | Mikawa | H01Q 3/24 |
| 2019/0167989 A1* | 6/2019 | Guyon | H01Q 7/00 |
| 2019/0175902 A1* | 6/2019 | Lee | A61B 5/0031 |
| 2020/0108252 A1* | 4/2020 | Zellmer | A61N 1/3752 607/116 |
| 2021/0378572 A1* | 12/2021 | Beker | A61N 1/36003 |
| 2022/0054246 A1* | 2/2022 | Forsell | A61B 5/0031 |

FOREIGN PATENT DOCUMENTS

| | | |
|---|---|---|
| JP | 2012-505022 A | 3/2012 |
| JP | WO2014/030317 A1 | 2/2014 |
| KR | 10-2011-0138357 A | 12/2011 |
| KR | 10-1360971 B1 | 2/2014 |
| KR | 10-1662594 B1 | 10/2016 |
| KR | 10-1907675 B1 | 10/2018 |

* cited by examiner

ND OBJECT STIMULATION APPARATUS

WIRELESS POWER RECEPTION AND OBJECT STIMULATION APPARATUS

CROSS-REFERENCE TO RELATED APPLICATIONS

This application claims the benefit under 35 USC § 119(a) of Korean Patent Application No. 10-2020-0045121, filed on Apr. 14, 2020, in the Korean Intellectual Property Office, the entire disclosure of which is incorporated herein by reference for all purposes.

BACKGROUND

1. Field

The following description relates to a wireless power reception and object stimulation apparatus.

2. Description of Related Art

An implantable device may be inserted into a human body and used for sensing biometric information or for treatment. Since the implantable device to be inserted into a human body, the implantable device may have a small volume. Also, since it may be difficult to attach or detach the implantable device inserted into the human body, power may be wirelessly supplied from outside the human body instead of replacing a battery of the implantable device. To wirelessly supply power to the implantable device inserted into the human body and simultaneously apply a stimulation signal to the human body, a wireless power reception device of the implantable device may include a coil for wirelessly receiving power and an electrode for electrical stimulation.

The above information disclosed in the Background section is possessed or acquired by inventors in a process of achieving the inventive concept, and is not necessarily a technology publicly disclosed prior to the filing date of the present application.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a wireless power reception apparatus includes: a first electrode including a coil shape; a second electrode including the coil shape; an electrode capacitor connected between the first electrode and the second electrode; an electrode signal transceiver connected to the first electrode and the second electrode; a power receiver connected to the first electrode and the second electrode, separately from the electrode signal transceiver; a resonant capacitor; and first capacitor and a second capacitor configured to connect a conducting line between the first electrode and the power receiver and a conducting line between the second electrode and the power receiver, wherein the first electrode and the second electrode are wound in the same direction.

The electrode signal transceiver may be configured to apply a low-frequency signal to the first electrode and the second electrode such that the electrode capacitor and the first and second capacitors are open.

The first electrode and the second electrode may be configured to apply an electrode signal to an object disposed between the first electrode and the second electrode, based on the low-frequency signal.

The first electrode and the second electrode may be configured to receive a high-frequency signal from a wireless power transmission apparatus such that the electrode capacitor is shorted.

The first electrode and the second electrode may be configured to form a single inductor, and the power receiver is charged with the high-frequency signal through a resonance by the inductor and the resonant capacitor.

The first electrode and the second electrode may be configured to receive the high-frequency signal from the wireless power transmission apparatus such that the first and second capacitors are shorted.

Either one or both of the first electrode and the second electrode may have a spiral structure.

Either one or both of the first electrode and the second electrode may have a mesh structure, and a conducting line between the mesh structure and the power receiver may include the coil shape enclosing the mesh structure.

Either one or both of the first electrode and the second electrode may include a spiral-mesh structure.

The first electrode and the second electrode may be bracket-shaped conductors with a width, and the first electrode and the second electrode may form a circle.

The apparatus may include a first inductor connected between the first electrode and the electrode signal transceiver; and a second inductor connected between the second electrode and the electrode signal transceiver.

The apparatus may include a first switch connected between the first electrode and the electrode signal transceiver; a second switch connected between the second electrode and the electrode signal transceiver; and a controller configured to: control the first switch and the second switch to be open in response to the first electrode and the second electrode receiving a high-frequency signal, and control the first switch and the second switch to be shorted in response to a low-frequency signal being applied to the first electrode and the second electrode.

The first capacitor may be connected between the first electrode and the power receiver; and the second capacitor may be connected between the second electrode and the power receiver.

The apparatus may include a housing comprising the electrode signal transceiver and the power receiver, wherein the electrode capacitor is disposed outside the housing.

The first electrode and the second electrode may be disposed on different sides of the wireless power reception apparatus, respectively.

The apparatus may include a housing comprising the electrode signal transceiver and the power receiver, wherein the electrode capacitor is disposed outside the housing.

The apparatus may include a controller configured to control the resonant capacitor to increase a reception voltage by a high-frequency signal received from a wireless power transmission apparatus.

The apparatus may include a controller configured to generate a response signal in response to a test signal received from a wireless power transmission apparatus, wherein a wireless power transmission apparatus may be configured to determine whether impedance matching is performed based on the generated response signal, and wherein the controller may be configured to receive a control signal generated based on a result of the determining by the wireless power transmission apparatus and to control the resonant capacitor based on the control signal.

Whether impedance matching is performed may be determined by a wireless power transmission apparatus based on a response signal generated in response to a test signal received from the wireless power transmission apparatus, and the first electrode and the second electrode may be configured to receive a resonant frequency signal selected based on a result of the determining by the wireless power transmission apparatus.

The electrode signal transceiver may be configured to communicate with an external communicator using a low-frequency signal.

The apparatus may be an object stimulation apparatus, the apparatus may include a membrane comprising the first electrode and the second electrode, and the electrode signal transceiver may be configured to apply an electrode signal to a beta cell through the first electrode and the second electrode.

In another general aspect, an object stimulation apparatus includes: a membrane comprising a first electrode and a second electrode; and an electrode signal transceiver connected to the first electrode and the second electrode and configured to apply an electrode signal to a beta cell through the first electrode and the second electrode.

Other features and aspects will be apparent from the following detailed description, the drawings, and the claims.

Figure 1:
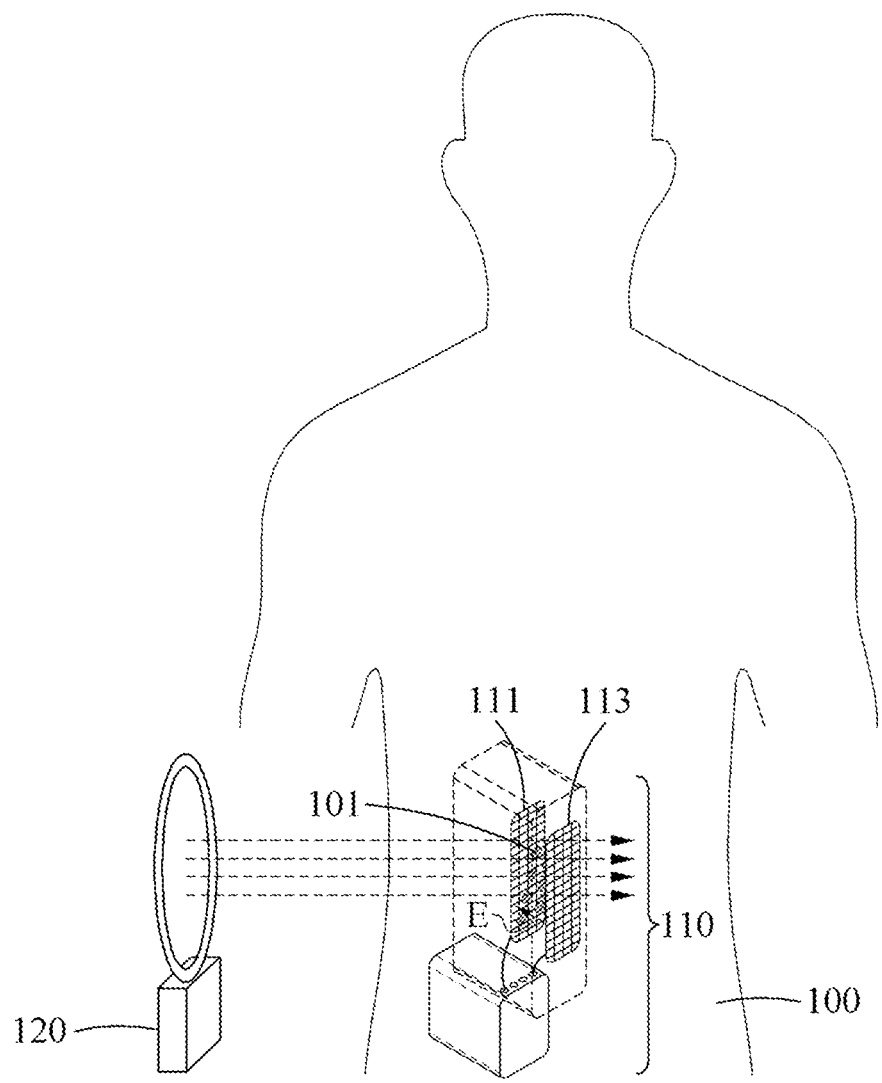
FIG. 1 illustrates an example of an operation of a wireless power reception apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Hereinafter, examples will be described in detail with reference to the accompanying drawings. The scope of the examples is not limited to the descriptions provided in the disclosure of this application. Various modifications may be made to the examples. Here, the examples are not construed as limited to the disclosure and should be understood to include all changes, equivalents, and replacements within the idea and the technical scope of the disclosure.

The terminology used herein is for the purpose of describing particular examples only and is not to be used to limit the disclosure of this application. As used herein, the singular forms "a", "an", and "the" are intended to include the plural forms as well, unless the context clearly indicates otherwise. As used herein, the term "and/or" includes any one and any combination of any two or more of the associated listed items. As used herein, the terms "include," "comprise," and "have" specify the presence of stated features, numbers, operations, elements, components, and/or combinations thereof, but do not preclude the presence or addition of one or more other features, numbers, operations, elements, components, and/or combinations thereof. The use of the term "may" herein with respect to an example or embodiment (for example, as to what an example or embodiment may include or implement) means that at least one example or embodiment exists where such a feature is included or implemented, while all examples are not limited thereto.

Unless otherwise defined, all terms including technical and scientific terms used herein have the same meaning as commonly understood by one of ordinary skill in the art to which this disclosure pertains consistent with and after an understanding of the present disclosure. It will be further understood that terms, such as those defined in commonly-used dictionaries, are to be interpreted as having a meaning that is consistent with their meaning in the context of the relevant art and the present disclosure, and are not to be interpreted in an idealized or overly formal sense unless expressly so defined herein.

When describing the examples with reference to the accompanying drawings, like reference numerals refer to like constituent elements and a repeated description related thereto will be omitted. In the description of examples, detailed description of well-known related structures or functions will be omitted when it is deemed that such description will cause ambiguous interpretation of the present disclosure.

Although terms of "first" or "second" are used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples. Also, the terms "first," "second," "A," "B," "(a)," "(b)," and the like may be used herein to describe components according to examples. Each of these terminologies is not used to define an essence, order or sequence of a corresponding component but used merely to distinguish the corresponding component from other component(s).

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

A component having a common function with a component included in one example is described using a like name in another example. Unless otherwise described, description made in one example may be applicable to another example and detailed description within a duplicate range is omitted.

FIG. 1 illustrates an example of an operation of a wireless power reception apparatus (e.g., a wireless power reception apparatus 110).

The wireless power reception apparatus 110 may use an electrode structure in wireless power reception, to reduce a volume of the wireless power reception apparatus 110. The wireless power reception apparatus 110 may share the electrode structure in transmission and reception of electrode signals and reception of wireless power, to reduce the volume of the wireless power reception apparatus 110. The wireless power reception apparatus 110 may use an electrode structure with a shape of a coil as an electrode or a coil based on a frequency, to reduce the volume of the wireless power reception apparatus 110. The wireless power reception apparatus 110 may be inserted into a human body 100.

The wireless power reception apparatus 110 may be, or may be applied to or included in, an implantable device. For example, the wireless power reception apparatus 110 may be, or may be applied to or included in, a deep brain stimulator (DBS), a cochlear implant, an implantable cardiac defibrillator (ICD), an insulin pump, and/or an artificial pancreas. However, the above implantable devices are merely an example, and the wireless power reception apparatus 110 may be, or may be applied to or included in, various types of implantable devices. Also, the wireless power reception apparatus 110 may be applied to an electronic device having a small volume, in addition to the implantable devices.

A small volume of an implantable device may be desired, to thereby reduce an invasiveness of the device, for example. An amount of current for electrical stimulation and an amount of received power may be proportional to a size of each of electrodes and a reception coil of the wireless power reception apparatus 110. Thus, the electrodes and reception coil of the wireless power reception apparatus 110 may have an effective or efficient space arrangement such that the wireless power reception apparatus 110 may receive the amount of current for the electrical stimulation and the amount of received power and, simultaneously, the volume of the wireless power reception apparatus 110 and/or the implantable device is small. To this end, the wireless power reception apparatus 110 may share an electrode structure in transmission and reception of electrode signals and reception of wireless power. In FIG. 1, the electrode structure may include at least two electrodes, for example, a first electrode 111 and a second electrode 113, each having a shape of a coil. The first electrode 111 and the second electrode 113 may be wound in a same direction. Coils may have various types of shapes, and may include, for example, a ring coil wound once, or a solenoid wound "n" times.

The wireless power reception apparatus 110 may use the first electrode 111 and the second electrode 113 for transmission and reception of electrode signals or for reception of wireless power, based on a frequency. The wireless power reception apparatus 110 may use the first electrode 111 and the second electrode 113 as coils or electrodes based on a frequency through an electrode capacitor connected in series between the first electrode 111 and the second electrode 113.

When a capacitor of wireless power reception apparatus 110 is open in response to a low-frequency signal in terms of impedance, the first electrode 111 and the second electrode 113 may be separated due to the open capacitor. The wireless power reception apparatus 110 may apply electrode signals to the first electrode 111 and the second electrode 113 that are separated, or may receive a data signal from an external device using the first electrode 111 and the second electrode 113 that are separated. When the capacitor is shorted (or closed) in response to a high-frequency signal in terms of impedance, the first electrode 111 and the second electrode 113 may be connected due to the shorted capacitor. When the first electrode 111 and the second electrode 113 each have a shape of a coil, the first electrode 111 and the second electrode 113 may function as a single coil when the first electrode 111 and the second electrode 113 are connected. Thus, an effect of further increasing a number of turns of an equivalent coil may be obtained due to the connection. The wireless power reception apparatus 110 may receive wireless power from a wireless power transmission apparatus (e.g., a wireless power transmission apparatus 120) using the first electrode 111 and the second electrode 113 that are connected together with a resonant capacitor (and a magnetic field H may be formed between the first electrode 111 and the second electrode 113, for example). The wireless power reception apparatus 110 may charge a battery with the received power.

The wireless power reception apparatus 110 may apply electrical stimulation to an object 101 disposed between the first electrode 111 and the second electrode 113 by applying a low-frequency signal. The first electrode 111 and the second electrode 113 may operate as separated electrodes in the low-frequency signal, and accordingly an electric field E may be formed between the first electrode 111 and the second electrode 113. By the electric field, the electrical stimulation may be applied to the object 101 disposed between the first electrode 111 and the second electrode 113. The object 101 may include, for example, a beta cell of an artificial pancreas.

The wireless power reception apparatus 110 may communicate with an external device using the first electrode 111 and the second electrode 113 by applying a low-frequency signal. An electrode signal transceiver included in the wireless power reception apparatus 110 may communicate with an external communication device using the low-frequency signal. The first electrode 111 and the second electrode 113 may operate as separated electrodes in the low-frequency signal, to receive an external data signal or transmit a data signal generated by the wireless power reception apparatus 110. The external device may include, for example, any one or more of other types of implantable devices inserted into the human body 100 or computing devices such as a computer, server, or smartphone external to the body 100.

Figure 2A:
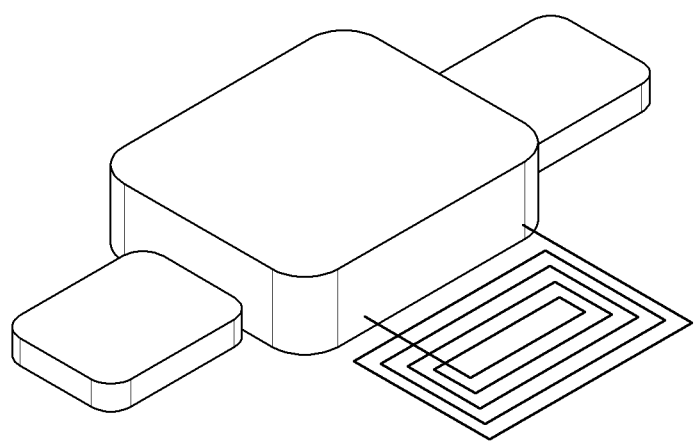
FIG. 2A illustrates an example of a typical wireless power receiver.
Figure 2B:
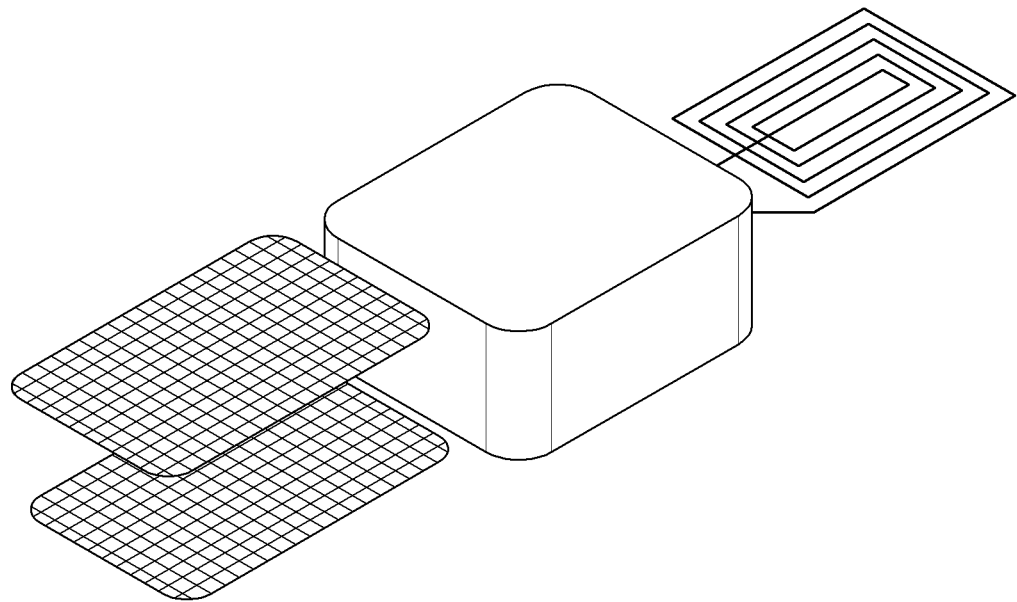
FIG. 2B illustrates another example of a typical wireless power receiver.
Figure 2C:
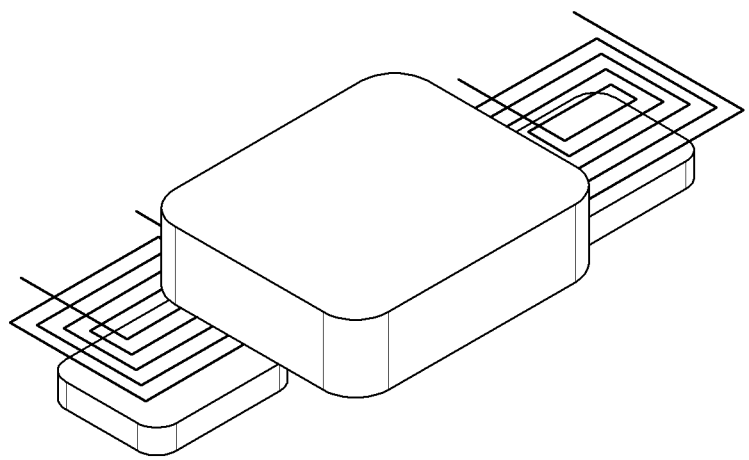
FIG. 2C illustrates an example of reducing an area occupied by the wireless power receiver of FIG. 2A by changing a structure of the wireless power receiver of FIG. 2A.
Figure 2D:
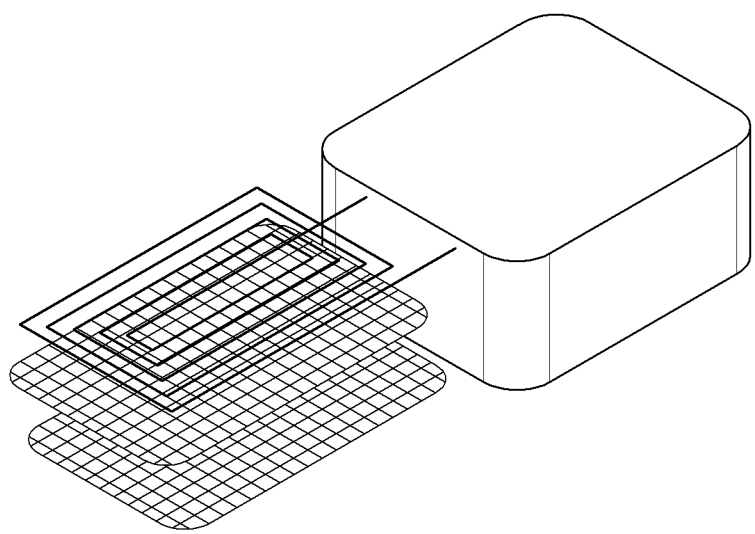
FIG. 2D illustrates an example of reducing an area occupied by the wireless power receiver of FIG. 2B by changing a structure of the wireless power receiver of FIG. 2B.

FIG. 2A illustrates an example of a typical wireless power receiver. FIG. 2B illustrates another example of a typical wireless power receiver. FIG. 2C illustrates an example of reducing an area occupied by the wireless power receiver of FIG. 2A by changing a structure of the wireless power receiver of FIG. 2A. FIG. 2D illustrates an example of reducing an area occupied by the wireless power receiver of FIG. 2B by changing a structure of the wireless power receiver of FIG. 2B.

Referring to FIG. 2A, two electrodes for transmission and reception of electrode signals of the wireless power receiver may be disposed on either side (e.g., opposite sides) of the typical wireless power receiver, and a coil for wireless power reception may be disposed on another side. Referring to FIG. 2B, two electrodes for transmission and reception of electrode signals of the wireless power receiver may be disposed on one side of the typical wireless power receiver, and a coil for wireless power reception may be disposed on an opposite side. Since the electrodes and the coils of the typical wireless power receivers occupy separate areas, as described above, the typical wireless power receivers of FIGS. 2A and 2B may be bulky and occupy a large area or volume.

FIG. 2C illustrates a structure in which coils may be superimposed on the two electrodes that are disposed on both the sides of the typical wireless power receiver in a structure of FIG. 2A. FIG. 2D illustrates a structure in which coils may be superimposed on the two electrodes that are disposed on one side of the typical wireless power receiver in a structure of FIG. 2B. However, since the electrodes are conductors, the electrodes prevent the coils from receiving wireless power. In other words, a performance of the typical wireless power reception apparatus, instead of only the area or volume thereof, may be reduced by the structures of FIGS. 2B and 2D.

Figure 3:
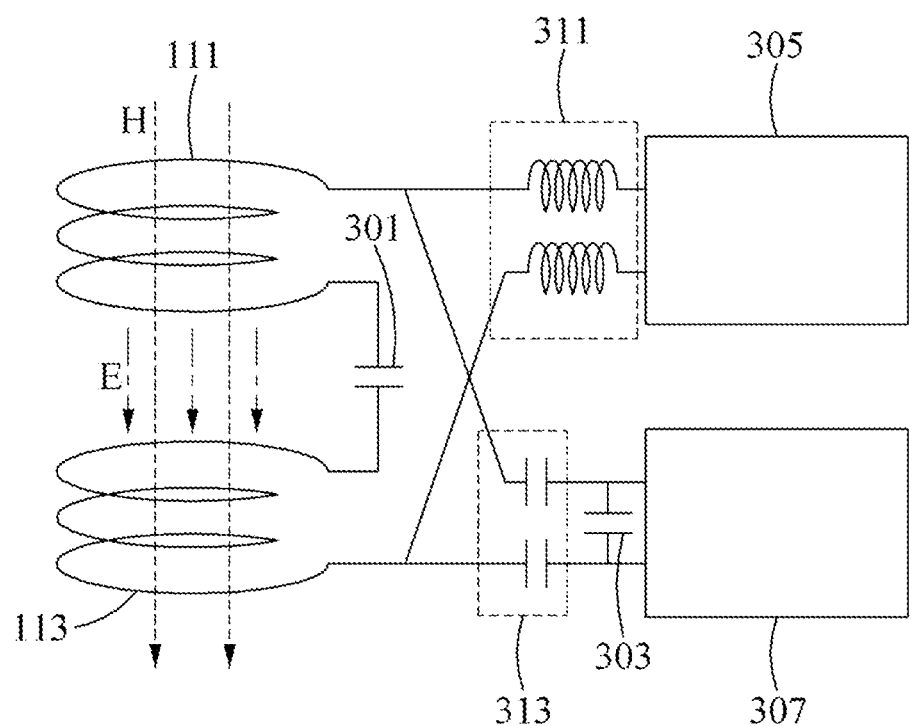
FIG. 3 illustrates an example of a configuration of a wireless power reception apparatus.

FIG. 3 illustrates an example of a configuration of a wireless power reception apparatus (e.g., the wireless power reception apparatus 110 of FIG. 1).

Referring to FIG. 3, the wireless power reception apparatus 110 may include the first electrode 111, the second electrode 113, an electrode capacitor 301 connected between the first electrode 111 and the second electrode 113, an electrode signal transceiver 305 connected to the first electrode 111 and the second electrode 113, a power receiver 307 connected to the first electrode 111 and the second electrode 113 separately from the electrode signal transceiver 305, a first capacitor and second capacitor 313 that connects a conducting line between the first electrode 111 and the power receiver 307 and a conducting line between the second electrode 113 and the power receiver 307, and a resonant capacitor 303 connected to the first capacitor and second capacitor 313 and the power receiver 307.

The first electrode 111 and the second electrode 113 may have a shape of a coil. The first electrode 111 and the second electrode 113 may be wound in the same direction. The shape of the coil may any one of various types of shapes, and may be, for example, a ring coil wound once, or a solenoid wound "n" times in which "n" is a natural number greater than or equal to "1".

The wireless power reception apparatus 110 may apply an electrode signal to a beta cell disposed between the first electrode 111 and the second electrode 113, through the first electrode 111 and the second electrode 113. Thus, the wireless power reception apparatus 110 may maintain or promote a function of the beta cell of an artificial pancreas.

When the wireless power reception apparatus 110 receives a high-frequency signal from a wireless power transmission apparatus through the first electrode 111 and the second electrode 113, the electrode capacitor 301 may be shorted (i.e., closed). When the electrode capacitor 301 is shorted, the wireless power reception apparatus 110 may form a single inductor through the first electrode 111 and the second electrode 113, and may charge the power receiver 307 with the high-frequency signal charge through resonance by the inductor and the resonant capacitor 303. The charged power receiver 307 may charge a battery of the power receiver 307, the wireless power reception apparatus 110, and/or the implantable device.

In an example, the wireless power reception apparatus 110 may further include a first inductor and second inductor 311 that strengthens an opening effect of the electrode signal transceiver 305. The first inductor 311 may be connected between the first electrode 111 and the electrode signal transceiver 305, and the second inductor 311 may be connected between the second electrode 113 and the electrode signal transceiver 305. The first inductor and second inductor 311 may be connected in parallel to the electrode signal transceiver 305.

In an example, the wireless power reception apparatus 110 may further include a first capacitor and second capacitor 313 to strengthen an opening effect of the power receiver 307. The first capacitor 313 may be connected between the first electrode 111 and the power receiver 307, and the second capacitor 313 may be connected between the second electrode 113 and the power receiver 307. The first capacitor and second capacitor 313 may be connected in parallel to the power receiver 307.

Figure 4A:
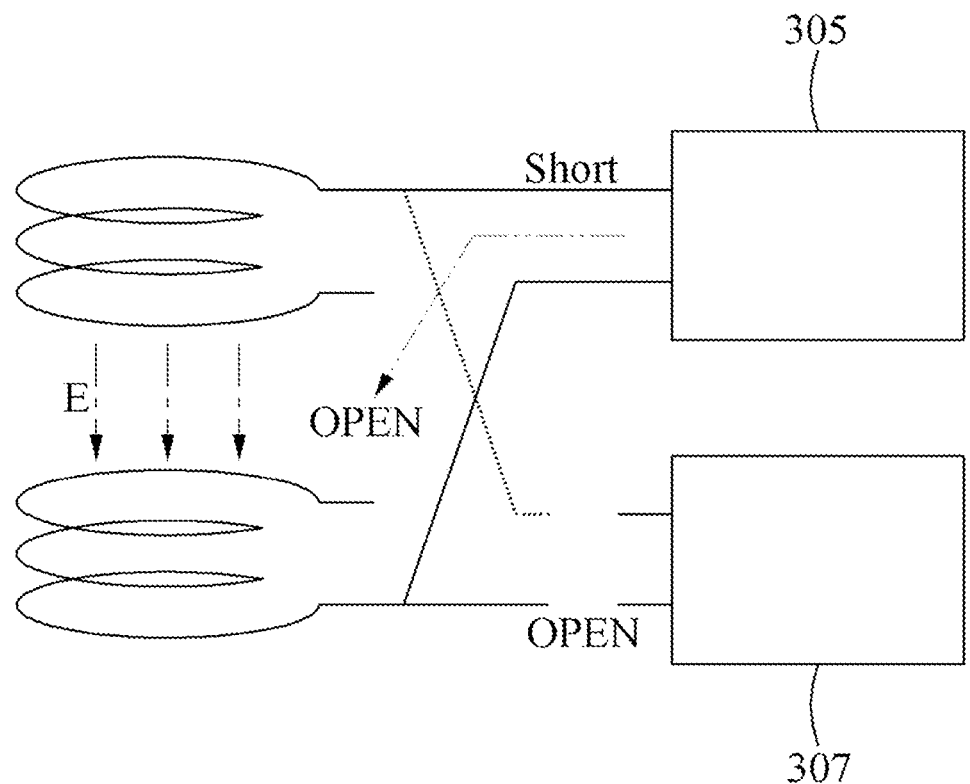
FIG. 4A illustrates an example of a wireless power reception apparatus in terms of impedance when a low-frequency signal is applied.
Figure 4B:
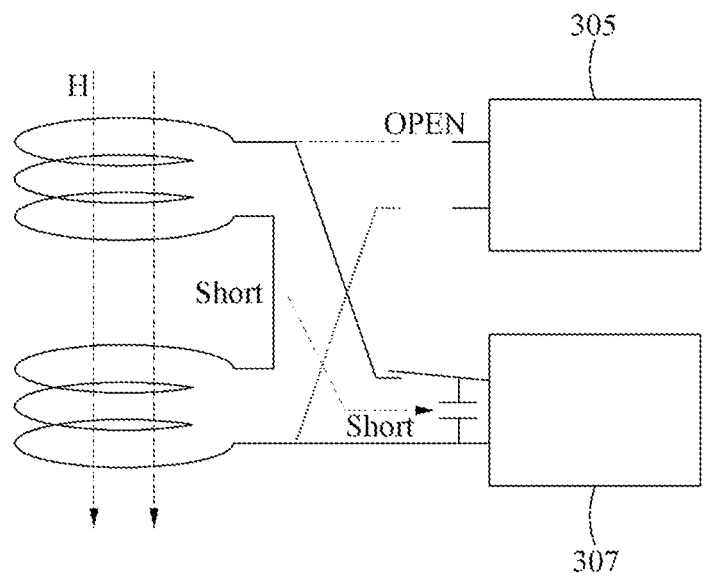
FIG. 4B illustrates an example of a wireless power reception apparatus in terms of impedance when a high-frequency signal is applied.

FIG. 4A illustrates an example of a wireless power reception apparatus (e.g., the wireless power reception apparatus 110 of FIG. 1) in terms of impedance when a low-frequency signal is applied. FIG. 4B illustrates an example of the wireless power reception apparatus 110 in terms of impedance when a high-frequency signal is applied. The wireless power reception apparatuses of FIGS. 4A and 4B may correspond to the wireless power reception apparatus of FIG. 3.

Referring to FIG. 4A, the wireless power reception apparatus 110 may include the first capacitor and second capacitor 313 that strengthen the opening effect of the power receiver 307. For example, when a low-frequency signal is applied, the first capacitor and second capacitor 313 may be open in terms of impedance. When the low-frequency signal is applied, the first inductor and second inductor 311 may be shorted in terms of impedance. When the first capacitor and second capacitor 313 are open, the power receiver 307 may not have an influence on the circuit, and a performance of transmission and reception of electrode signals of the electrode signal transceiver 305 may be enhanced. Although the power receiver 307 may act as equivalent impedance, the performance of transmission and reception of electrode signals may be enhanced by excluding the power receiver 307 from the entire circuit.

Referring to FIG. 4B, the wireless power reception apparatus 110 may include the first inductor and second inductor 311 that strengthen the opening effect of the electrode signal transceiver 305. For example, when a high-frequency signal is applied, the first inductor and second inductor 311 may be open in terms of impedance. When the high-frequency signal is applied, the first capacitor and second capacitor 313 may be shorted in terms of impedance. When the first inductor and second inductor 311 are open, the electrode signal transceiver 305 may not have an influence on the circuit, and a wireless power reception performance of the power receiver 307 may be enhanced. Although the electrode signal transceiver 305 may act as equivalent impedance, impedance matching by the resonant capacitor 303 and an equivalent inductor formed by the first electrode 111 and the second electrode 113 may be accurately performed by excluding the electrode signal transceiver 305 from the entire circuit.

Figure 5A:
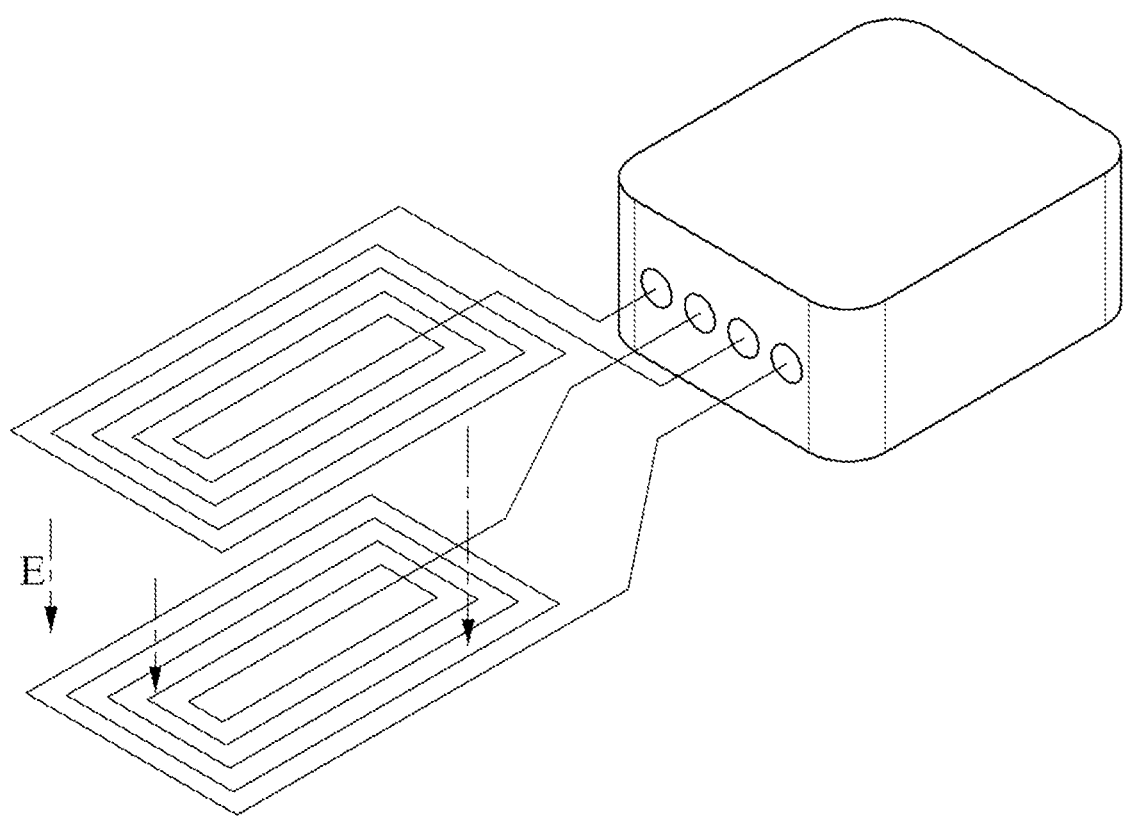
FIG. 5A illustrates an example of a spiral electrode of a wireless power reception apparatus.
Figure 5B:
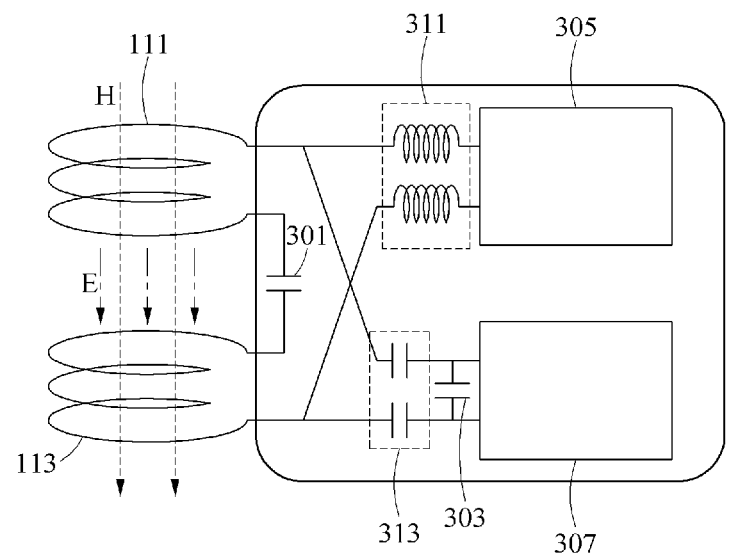
FIG. 5B illustrates an example of a position of an electrode capacitor of a wireless power reception apparatus.
Figure 5C:
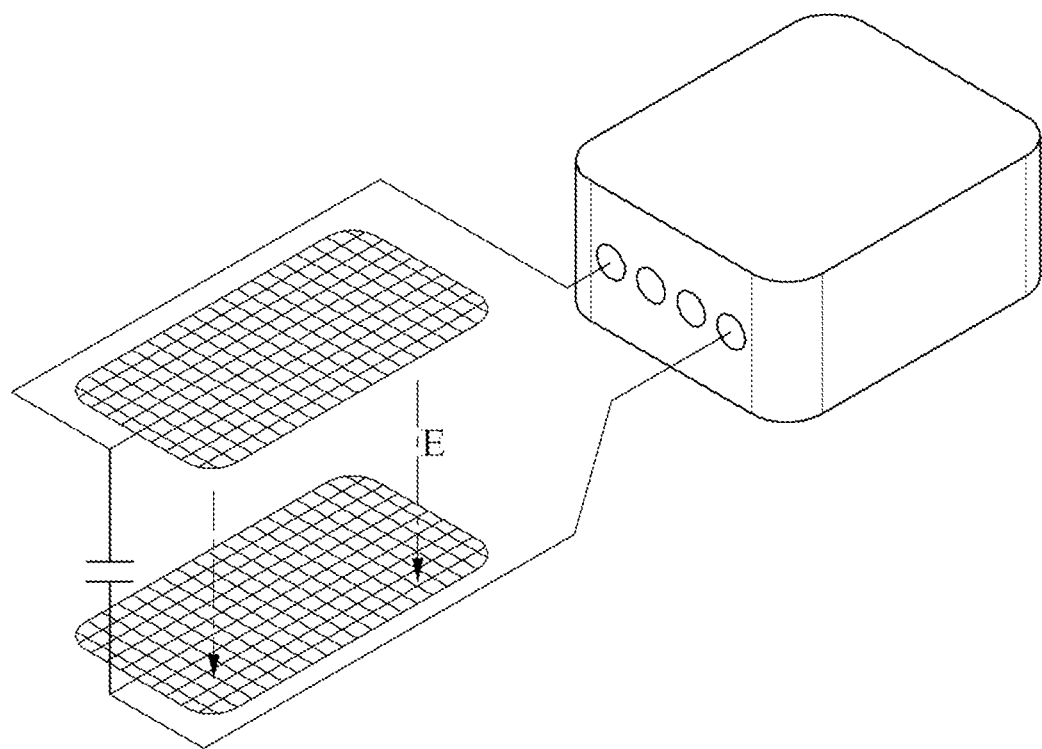
FIG. 5C illustrates an example of a mesh electrode of a wireless power reception apparatus.
Figure 5D:
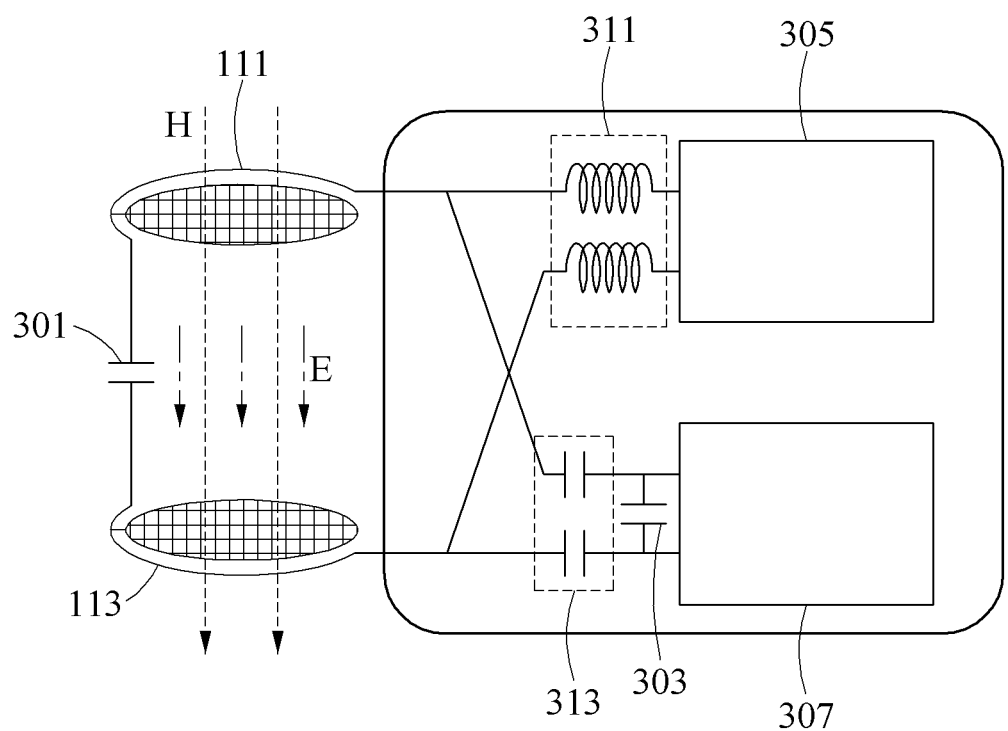
FIG. 5D illustrates an example of a position of an electrode capacitor of a wireless power reception apparatus.
Figure 5E:
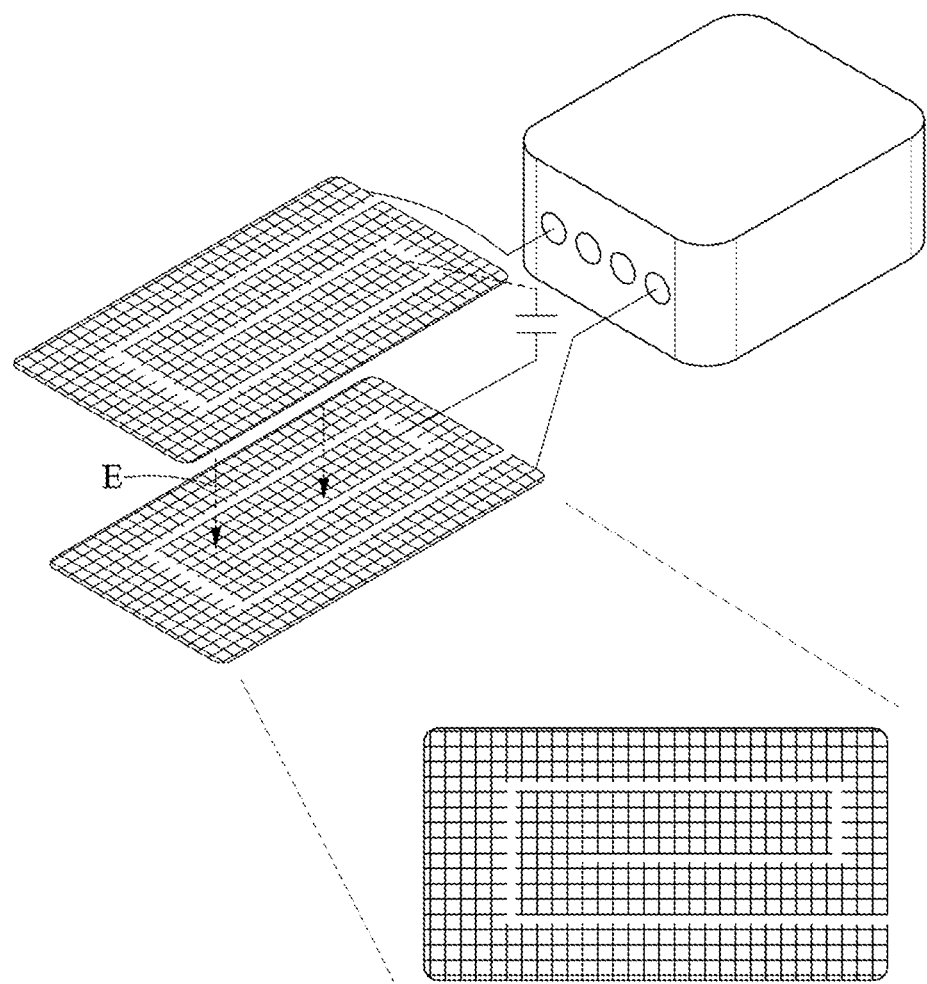
FIG. 5E illustrates an example of a spiral-mesh electrode of a wireless power reception apparatus.
Figure 5F:
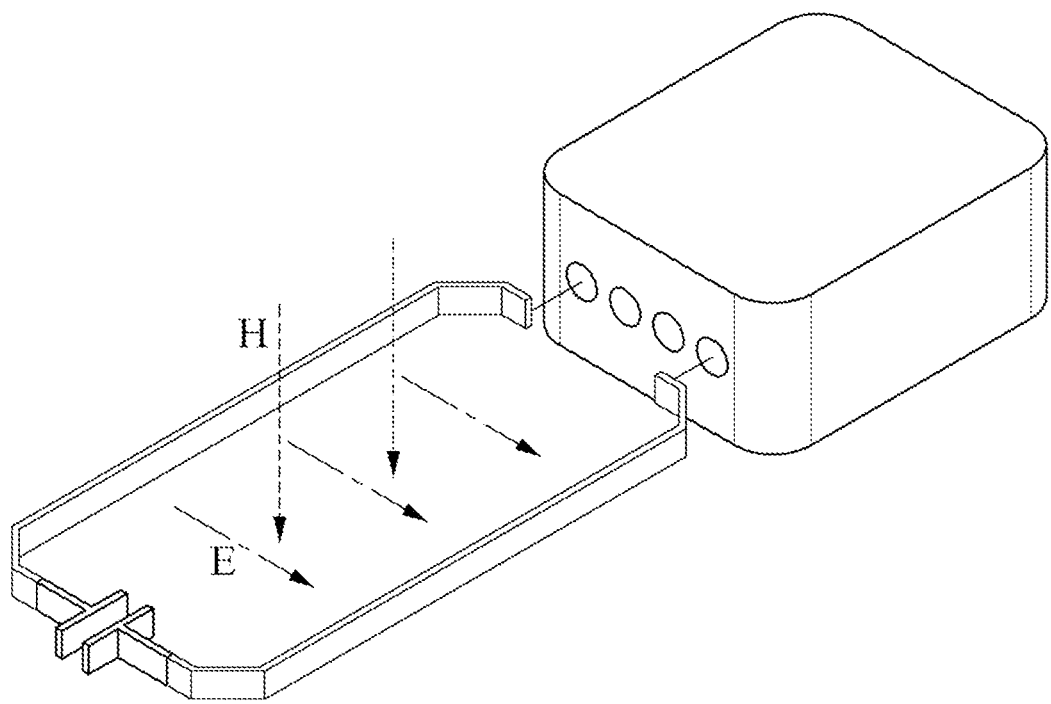
FIG. 5F illustrates an example of a ribbon electrode of a wireless power reception apparatus.

FIG. 5A illustrates an example of a spiral electrode of a wireless power reception apparatus (e.g., the wireless power reception apparatus 110 of FIG. 1). FIG. 5B illustrates an example of a position of an electrode capacitor of a wireless power reception apparatus (e.g., the wireless power reception apparatus of FIG. 5A). FIG. 5C illustrates an example of a mesh electrode of a wireless power reception apparatus (e.g., the wireless power reception apparatus 110 of FIG. 1). FIG. 5D illustrates an example of a position of an electrode capacitor of a wireless power reception apparatus (e.g., the wireless power reception apparatus of FIG. 5C). FIG. 5E illustrates an example of a spiral-mesh electrode of a wireless power reception apparatus (e.g., the wireless power reception apparatus 110 of FIG. 1). FIG. 5F illustrates an example of a ribbon electrode of a wireless power reception apparatus (e.g., the wireless power reception apparatus 110 of FIG. 1).

Referring to FIGS. 5A and 5B, a first electrode 111 and/or a second electrode 113 of the wireless power reception apparatus 110 may have a spiral structure. The first electrode 111 or the second electrode 113 having the spiral structure may be wound in the same direction. Due to a large number of turns in the spiral structure, the wireless power reception apparatus 110 may have enhanced performance when charge the power receiver 307 using the high-frequency signal.

In response to a low-frequency signal, an electrode capacitor 301 may be open, and the first electrode 111 and the second electrode 113 may vertically form an electric field. In response to a high-frequency signal, the electrode capacitor 301 may be shorted, the first electrode and the second electrode may form a single coil, and a magnetic field may be vertically formed.

FIG. 5B illustrates a concept of the wireless power reception apparatus 110 of FIG. 5A. For example, the electrode capacitor 301 may connect the first electrode 111 and the second electrode 113 in series and may be located in a housing. In this example, the housing may include four ports. Also, the housing may include the electrode signal transceiver 305 and the power receiver 307.

Referring to FIGS. 5C and 5D, the first electrode 111 and/or the second electrode 113 of the wireless power reception apparatus 110 may have a mesh structure. A conducting line between the mesh structure and the power receiver may have a shape of a coil enclosing the mesh structure. By the conducting line having the shape of the coil enclosing the mesh structure, wireless power may be received. Since the mesh structure appears as a single conductor in a low frequency, a better performance as an electrode may be achieved.

In response to a low-frequency signal, the electrode capacitor 301 may be open, and the first electrode 111 and the second 113 electrode may vertically form an electric field. In response to a high-frequency signal, the electrode capacitor 301 may be shorted, the first electrode and the second electrode may form a single coil, and a magnetic field may be vertically formed.

FIG. 5D illustrates a concept of the wireless power reception apparatus 110 of FIG. 5C. For example, the electrode capacitor 301 may connect the first electrode 111 and the second electrode 113 in series and may be located outside the housing. In this example, the housing may include two ports, and thus a manufacturing process may be simplified and a manufacturing unit cost may be reduced. Also, the housing may include the electrode signal transceiver 305 and the power receiver 307.

Referring to FIG. 5E, the first electrode 111 and/or the second electrode 113 of the wireless power reception apparatus 110 may have a spiral-mesh structure. The spiral-mesh structure may be a structure in which a conducting line forming a spiral structure has a width greater than or equal to a predetermined value and in which a conducting line is formed with a mesh shape. The spiral-mesh structure may implement a larger number of turns than that of the mesh structure, and a performance as a coil may be further enhanced compared to the mesh structure.

Referring to FIG. 5F, the first electrode 111 and the second electrode 113 of the wireless power reception apparatus 110 may be bracket-shaped conductors with a width. The first electrode and the second electrode may form a circle together. In response to a low-frequency signal, electrode capacitor 301 may be open, and the first electrode 111 and the second electrode 113 may horizontally form an electric field. In response to a high-frequency signal, the electrode capacitor 301 may be shorted, the first electrode and the second electrode may form a single coil, and a magnetic field may be vertically formed.

Figure 6A:
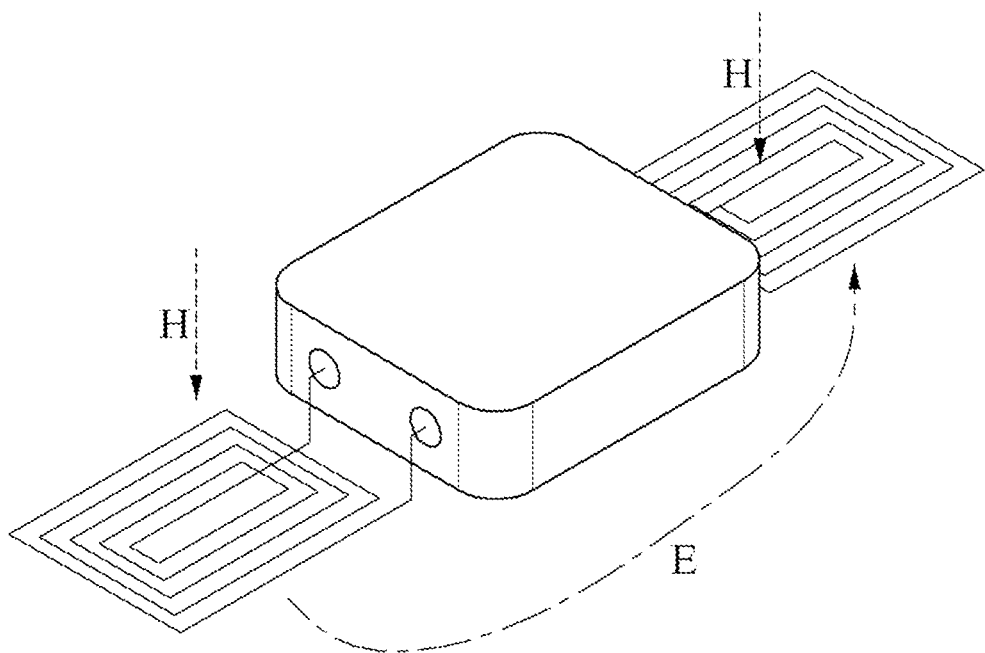
FIG. 6A illustrates an example of a horizontal electrode structure of a wireless power reception apparatus.
Figure 6B:
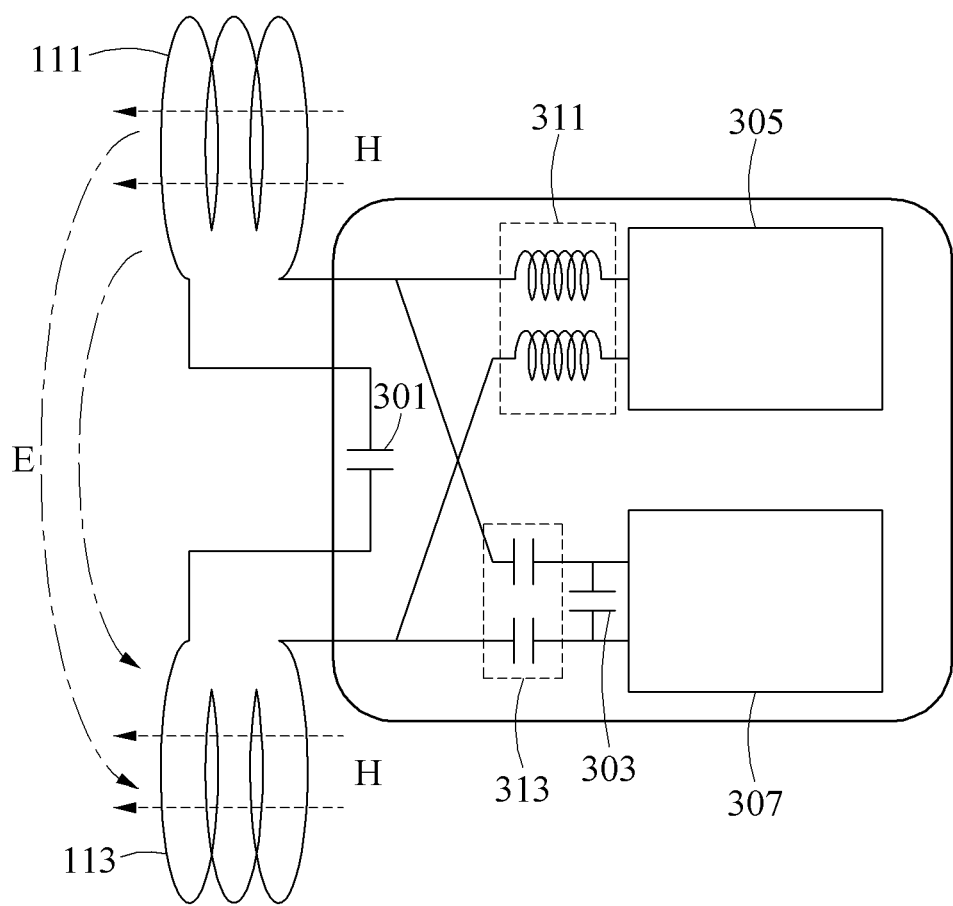
FIG. 6B illustrates an example of an internal structure of a wireless power reception apparatus.
Figure 6C:
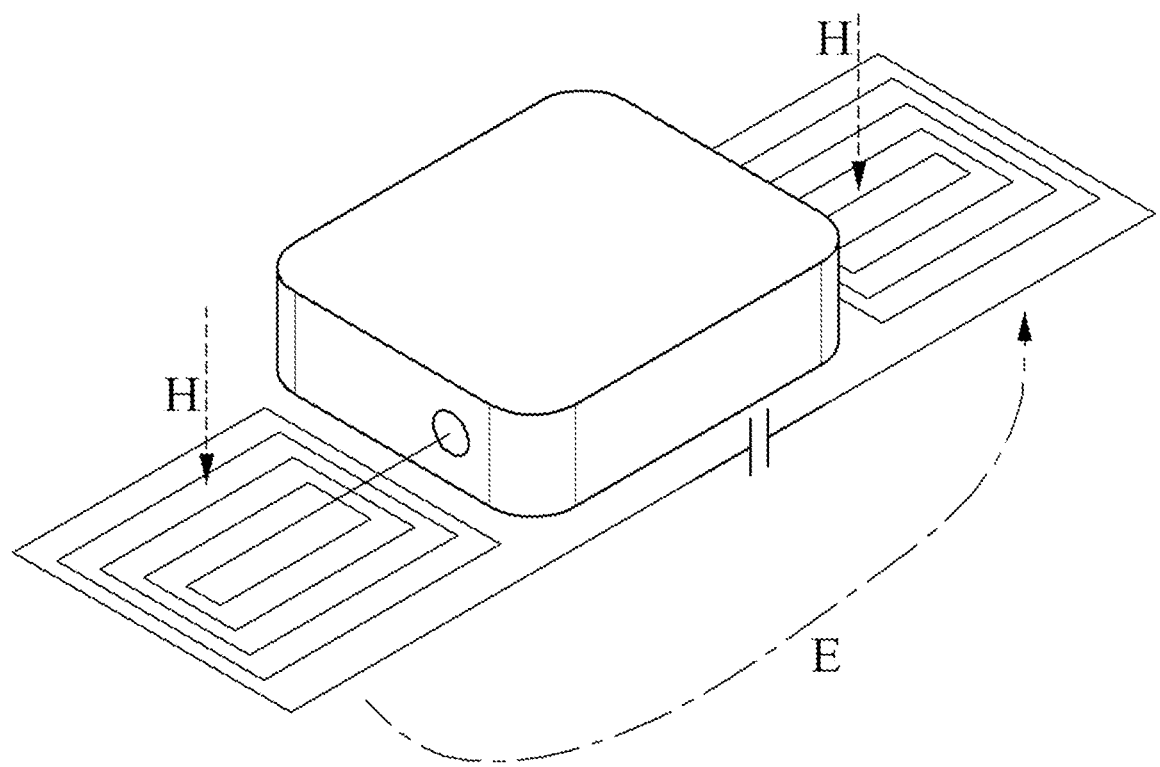
FIG. 6C illustrates another example of a horizontal electrode structure of a wireless power reception apparatus.
Figure 6D:
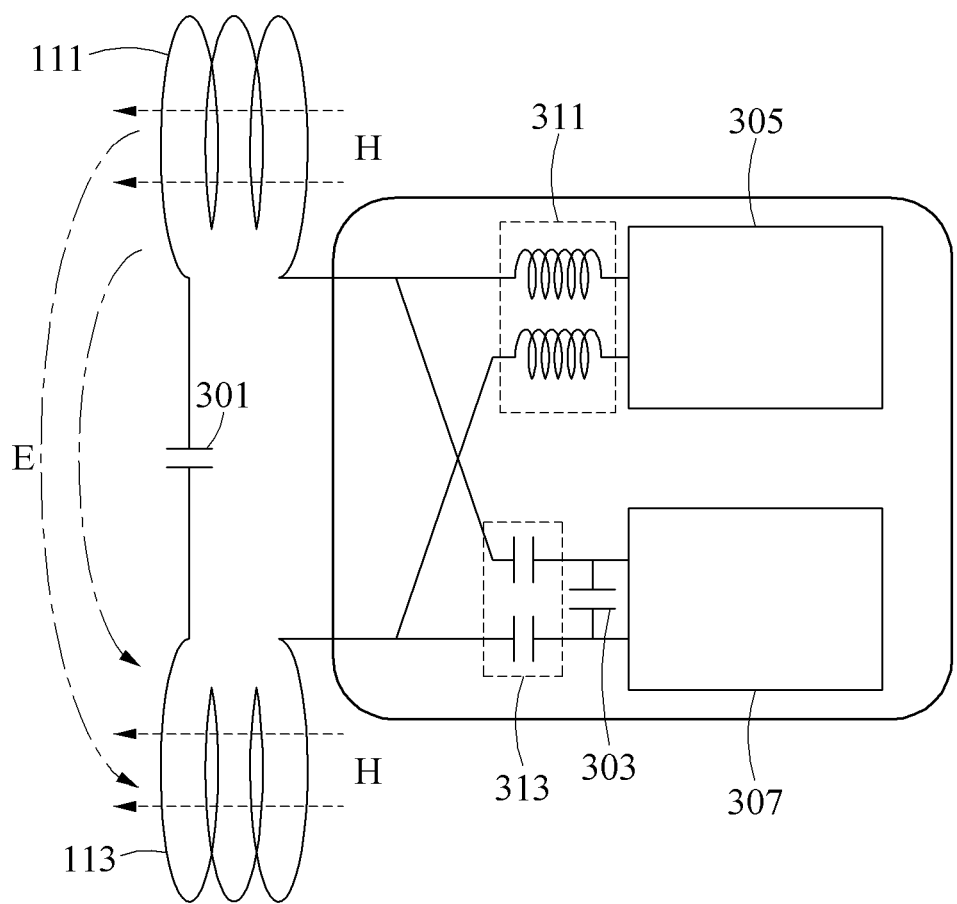
FIG. 6D illustrates an example of an internal structure of a wireless power reception apparatus.

FIG. 6A illustrates an example of a horizontal electrode structure of a wireless power reception apparatus 110. FIG. 6B illustrates an example of an internal structure of a wireless power reception apparatus (e.g., the wireless power reception apparatus 110 of FIG. 6A). FIG. 6C illustrates another example of a horizontal electrode structure of a wireless power reception apparatus 110. FIG. 6D illustrates an example of an internal structure of a wireless power reception apparatus (e.g., the wireless power reception apparatus 110 of FIG. 6C).

Referring to FIG. 6A, a first electrode 111 and a second electrode 113 may be disposed on either side (e.g., opposite sides) of the wireless power reception apparatus 110, respectively. In response to a low-frequency signal, the electrode capacitor 301 may be open, and the first electrode 111 and the second electrode 113 may horizontally form an electric field. In response to a high-frequency signal, the electrode capacitor 301 may be shorted, the first electrode 111 and the second electrode 113 may form a single coil, and a magnetic field may be vertically formed.

FIG. 6B illustrates an example in which the electrode capacitor of the wireless power reception apparatus 110 of FIG. 6A is located in a housing. The housing may include four ports. Also, the housing may include the electrode signal transceiver 305 and the power receiver 307.

Referring to FIG. 6C, the first electrode 111 and the second electrode 113 may be disposed on either side (e.g., opposite sides) of the wireless power reception apparatus 110, respectively. In response to a low-frequency signal, the electrode capacitor 301 may be open, and the first electrode 111 and the second electrode 113 may horizontally form an electric field. In response to a high-frequency signal, the electrode capacitor 301 may be shorted, the first electrode 111 and the second electrode 113 may form a single coil, and a magnetic field may be vertically formed.

FIG. 6D illustrates an example in which the electrode capacitor 301 of the wireless power reception apparatus 110 of FIG. 6C is located outside a housing. The housing may include two ports, and thus a manufacturing process may be simplified and a manufacturing unit cost may be reduced. The housing may include the electrode signal transceiver 305 and a power receiver 307.

Figure 7:
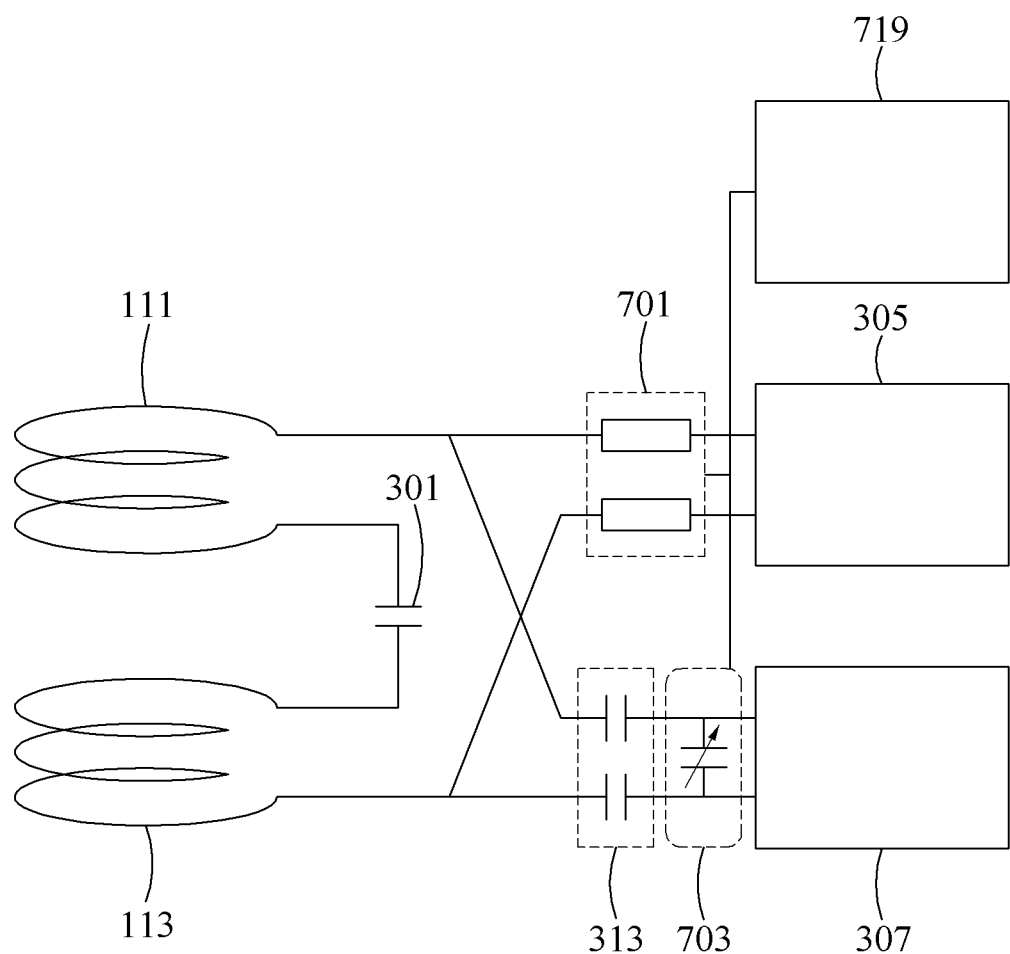
FIG. 7 illustrates an example of impedance matching by a wireless power reception apparatus.

FIG. 7 illustrates an example of impedance matching by a wireless power reception apparatus (e.g., the wireless power reception apparatus 110).

Impedance matching may be performed based on impedance information acquired by impedance measurement of a receiver. In the following description, a wireless power transmission apparatus may be referred to as a "transmitter", and a wireless power reception apparatus 110 may be referred to as a "receiver".

The wireless power reception apparatus 110 may determine whether impedance matching is performed, to receive wireless power. The wireless power reception apparatus 110 may measure a magnitude of received power, to determine whether the impedance matching is performed. The wireless power reception apparatus 110 may include a controller 719. In an example, the controller 719 may be or include one or more processors configured to perform the operations of the controller 719. The controller 719 may control a resonant capacitor 703 so that reception voltage (e.g., voltage received by the power receiver 307) by a high-frequency signal received from the wireless power transmission apparatus may be maximized or increased.

In response to a high-frequency signal transmitted by the wireless power transmission apparatus, the electrode capacitor 301 and the first capacitor and second capacitor 313 may be shorted. The first electrode 111 and the second electrode 113 may operate as a single coil. The impedance matching may be performed by a resonant capacitor 703 and inductance of a coil formed by the first electrode 111 and the second electrode 113. For the impedance matching, the resonant capacitor 703 may include a varactor, or a cap bank. Capacitance of the resonant capacitor 703 may be set so that voltage of a reception coil (e.g., the first electrode 111 and the second electrode 113) may be maximized. The resonant capacitor 703 may correspond to the resonant capacitor 303, in a non-limiting example.

The wireless power reception apparatus 110 may further include a component 701 to strengthen an opening effect of an electrode signal transceiver 305. For example, the component 701 may include an inductor or a switch. The wireless power reception apparatus 110 may strengthen an opening effect of a power receiver 307 by adding the first capacitor and second capacitor 313. The component 701 may correspond to the first inductor and second inductor 311, in a non-limiting example.

Figure 8:
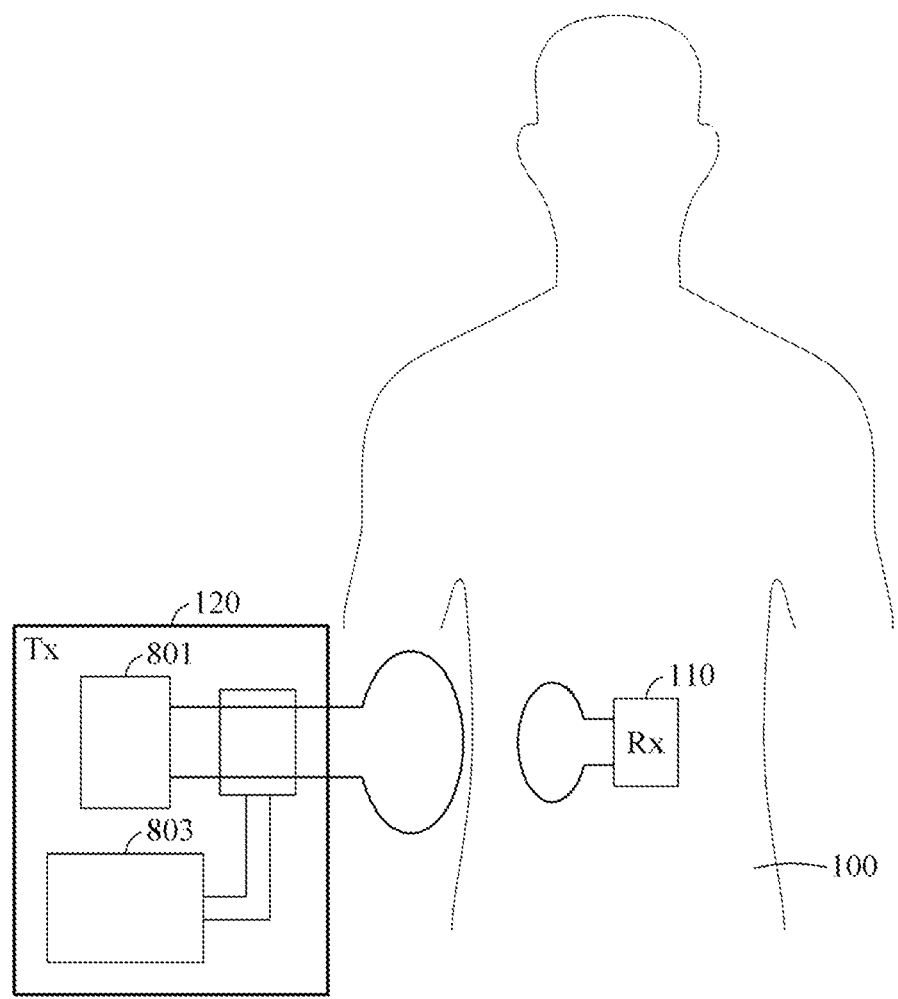
FIG. 8 illustrates an example of impedance matching of a wireless power reception apparatus by a wireless power transmission apparatus.

FIG. 8 illustrates an example of impedance matching by a wireless power transmission apparatus (e.g., the wireless power transmission apparatus 120).

Impedance matching may be performed based on impedance information acquired by impedance measurement of a transmitter.

In an example, a wireless power reception apparatus 110 may include a controller (e.g., the controller 719). The wireless power transmission apparatus 120 may transmit a test signal to the wireless power reception apparatus 110 using a signal transceiver 801. The test signal may have a predetermined frequency. In response to the test signal being received from the wireless power transmission apparatus 120, a response signal may be generated in the wireless power reception apparatus 110 (e.g., by a control of the controller 719 and/or by the electrode signal transceiver 305).

The wireless power transmission apparatus 120 may determine whether impedance matching is performed based on the response signal, using a controller 803. To determine an impedance matching state at a receiver, the wireless power transmission apparatus 120 may measure input impedance of a transmission coil. Referring to Equation 1 below, for example, the input impedance of the transmission coil includes a sum of impedance $R_{RX}+j\omega L_{Rx}$ of a reception coil and a load $Z_L$ of the reception coil. When a sum of imaginary values of the impedance $R_{RX}+j\omega L_{Rx}$ and the load $Z_L$ is zero, a resonance state may occur.

$$Z_{in} = R_{Tx} + j\omega L_{Tx} + \frac{K_m^2}{R_{Rx} + j\omega L_{Rx} + Z_L} \quad \text{Equation 1}$$

$$K_m^2 = k^2 \omega^2 L_{Tx} L_{Rx}$$

-continued k: coupling coefficient

ω: radian frequency $L_{Tx}$, $L_{Rx}$: inductances

The wireless power transmission apparatus 120 may calculate capacitance of a resonant capacitor at which the sum of the imaginary values of the impedance $R_{RX}+j\omega L_{Rx}$ and the load $Z_L$ in Equation 1 is zero. The controller 803 of the wireless power transmission apparatus 120 may control the signal transceiver 801 to transmit a control signal including information of the calculated capacitance to the receiver, and may adjust resonant capacitance of the receiver. As described above, the wireless power transmission apparatus 120 may transmit the control signal to the wireless power reception apparatus 110 based on a determination result of the impedance matching.

The wireless power reception apparatus 110 may receive a control signal generated based on the determination result of the wireless power transmission apparatus 120. The controller 719 may control the resonant capacitor 703 based on the control signal.

In another example, the wireless power transmission apparatus 120 may select a frequency at which impedance matching is achieved. The wireless power transmission apparatus 120 may measure the input impedance of the transmission coil while changing a transmission frequency, and may select a frequency at which impedance of the reception coil is matched. The wireless power transmission apparatus 120 may set the selected frequency as a frequency of a transmission signal.

Based on a response signal generated in response to the test signal received from the wireless power transmission apparatus 120, whether impedance matching is performed may be determined by the wireless power transmission apparatus 120. The wireless power transmission apparatus 120 may determine a frequency at which impedance matching is achieved. The wireless power transmission apparatus 120 may transmit a signal of the determined frequency to the wireless power reception apparatus 110. The first electrode and the second electrode of the wireless power reception apparatus 110 may receive a resonant frequency signal selected based on a determination result of the wireless power transmission apparatus 120.

Figure 9A:
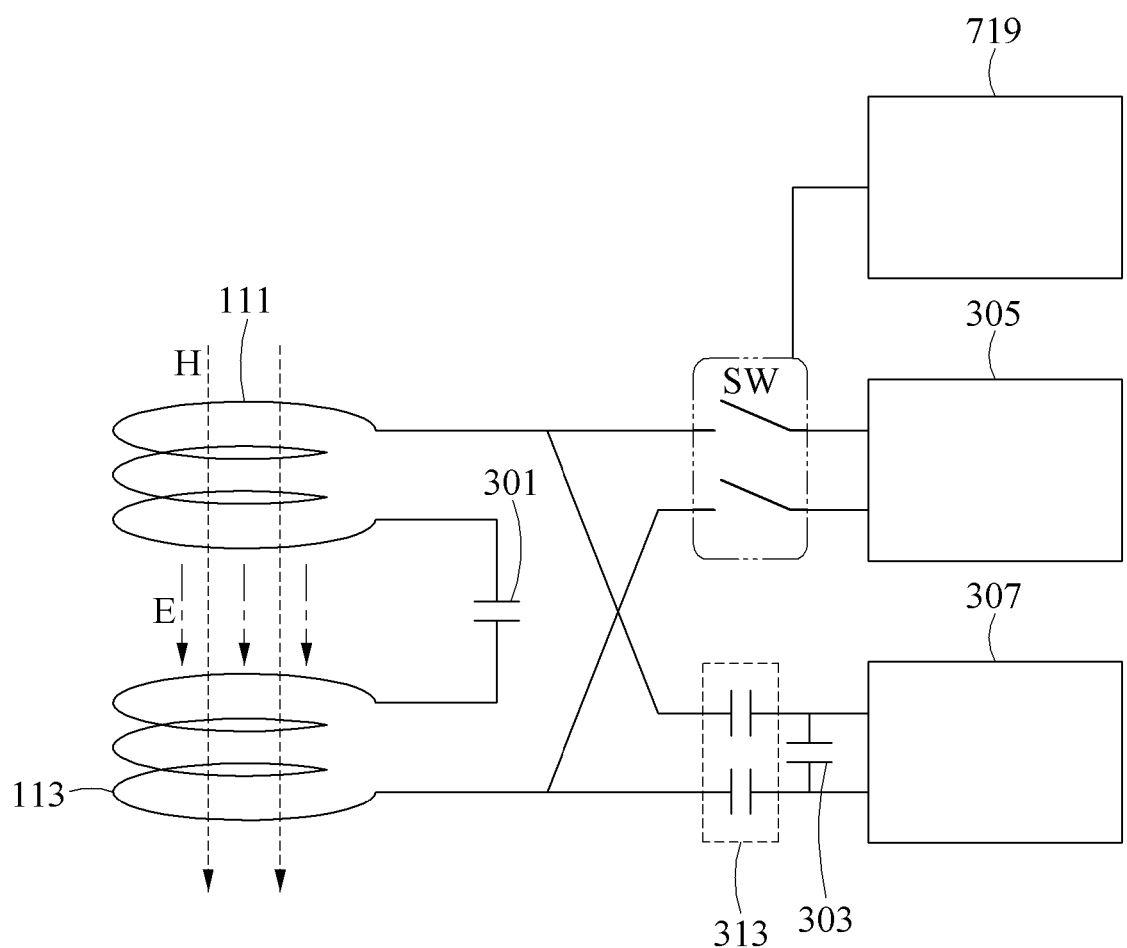
FIG. 9A illustrates an example of a wireless power reception apparatus to which a switch is applied.
Figure 9B:
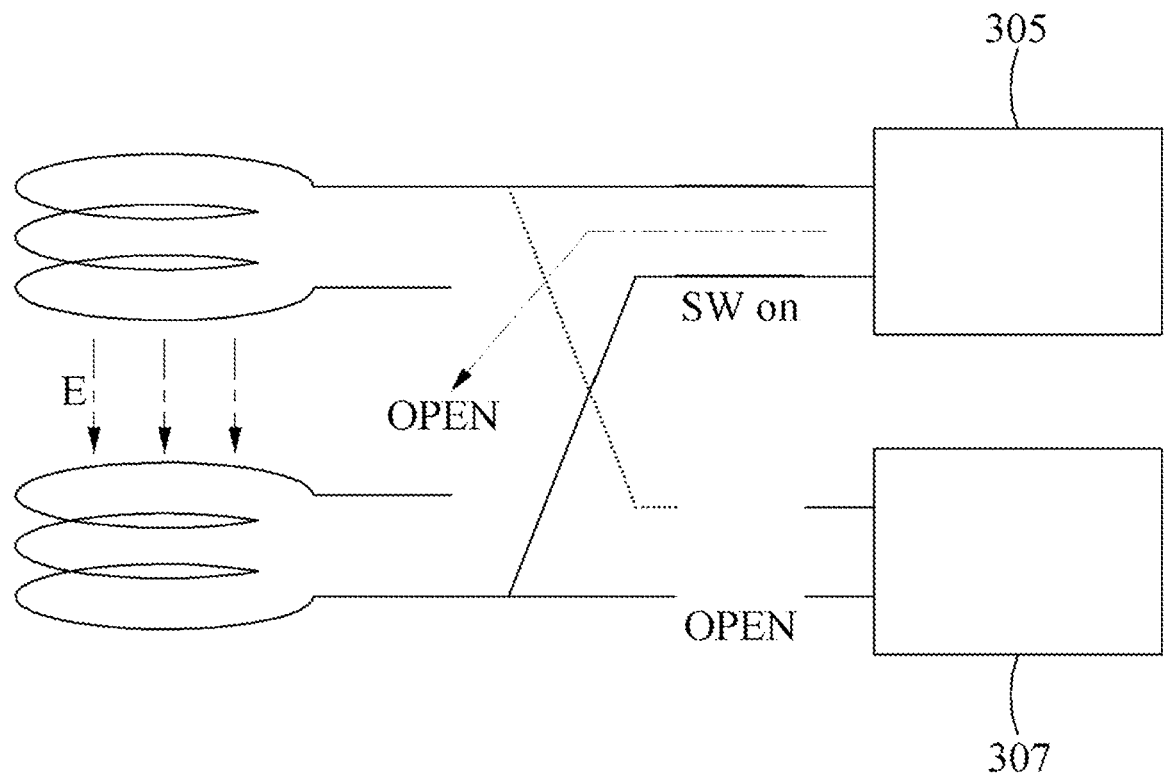
FIG. 9B illustrates an example of a wireless power reception apparatus in terms of impedance when a low-frequency signal is applied.
Figure 9C:
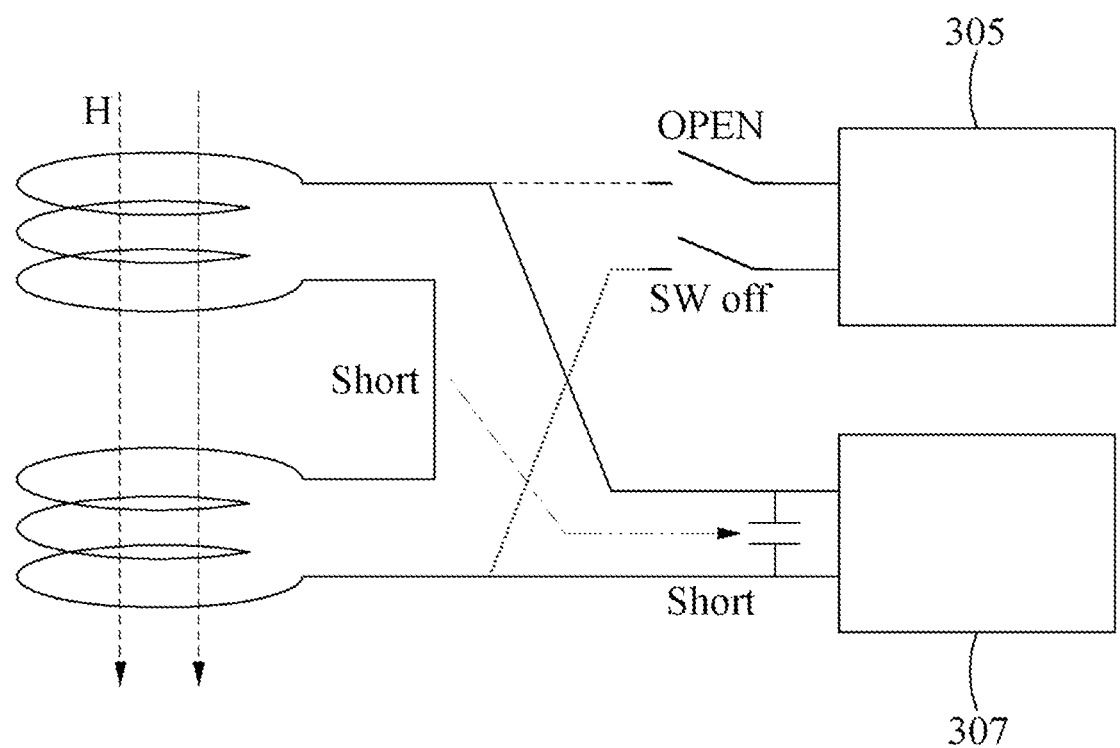
FIG. 9C illustrates an example of a wireless power reception apparatus in terms of impedance when a high-frequency signal is applied.

FIG. 9A illustrates an example of a wireless power reception apparatus 110 to which a switch is applied. FIG. 9B illustrates an example of a wireless power reception apparatus (e.g., the wireless power reception apparatus 110 of FIG. 9A) in terms of impedance when a low-frequency signal is applied. FIG. 9C illustrates an example of a wireless power reception apparatus (e.g., the wireless power reception apparatus 110 of FIG. 9A) in terms of impedance when a high-frequency signal is applied.

Referring to FIG. 9A, the wireless power reception apparatus 110 may strengthen an opening effect of an electrode signal transceiver 305 using a switch SW instead of using an inductor. To this end, the wireless power reception apparatus 110 may include a controller 719. In an example, the controller 719 may be or include one or more processors configured to perform the operations of the controller 719. A first switch of the switch SW may be connected between the first electrode 111 and the electrode signal transceiver 305, and a second switch of the switch SW may be connected between the second electrode 113 and the electrode signal transceiver 305.

When the first electrode and the second electrode receive high-frequency signals, the controller 719 may control the first switch and the second switch to be open. Referring to FIG. 9C, in response to a high-frequency signal, a first capacitor and a second capacitor 313 disposed in front of the resonant capacitor 303 and a power receiver 307 may be shorted. A switch disposed in front of the electrode signal transceiver 305 may be open.

When low-frequency signals are applied to the first electrode 111 and the second electrode 113, the controller may control the first switch and the second switch to be shorted. Referring to FIG. 9B, in response to a low-frequency signal, a first capacitor and a second capacitor 313 disposed in front of the resonant capacitor 303 and a power receiver 307 may be open. A switch disposed in front of the electrode signal transceiver 305 may be shorted.

Figure 10:
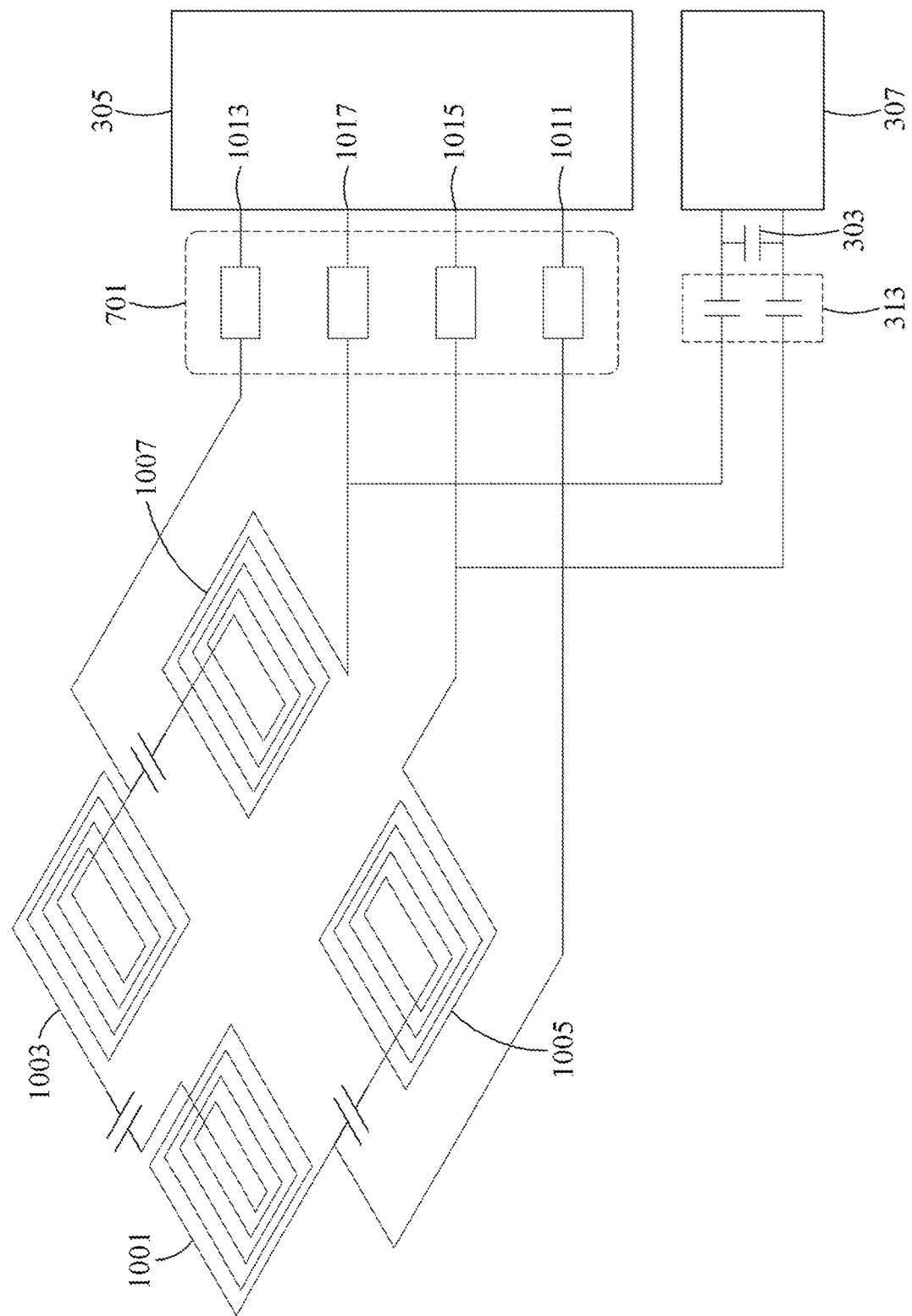
FIG. 10 illustrates an example of a wireless power reception apparatus including four electrodes.

FIG. 10 illustrates an example of a wireless power reception apparatus (e.g., the wireless power reception apparatus 110) including four electrodes.

The wireless power reception apparatus 110 may include a plurality of electrodes. The wireless power reception apparatus 110 may select two electrodes among the plurality of electrodes and may use the selected electrodes to transmit or receive electrode signals.

Referring to FIG. 10, the four electrodes may be connected to the wireless power reception apparatus 110. Electrodes 1001, 1003, 1005, and 1007 may be connected to ports 1011, 1013, 1015, and 1017, respectively. Except for a pair of electrodes, each electrode capacitor may be connected in series between the plurality of electrodes.

The plurality of electrodes may have a shape of a coil. The electrodes may be wound in the same direction. When an electrode capacitor is shorted in response to a high-frequency signal, the plurality of electrodes may operate as a single coil.

To strengthen an opening effect of an electrode signal transceiver 305, the wireless power reception apparatus 110 may include a component 701. The component 701 may include an inductor or a switch. The component 701 may be open in response to a high-frequency signal, and may be shorted in response to a low-frequency signal.

To strengthen the opening effect of the electrode signal transceiver 305, the wireless power reception apparatus 110 may include a first capacitor and second capacitor 313. The first capacitor and the second capacitor 313 may be open in response to a low-frequency signal, and may be shorted in response to a high-frequency signal.

Figure 11A:
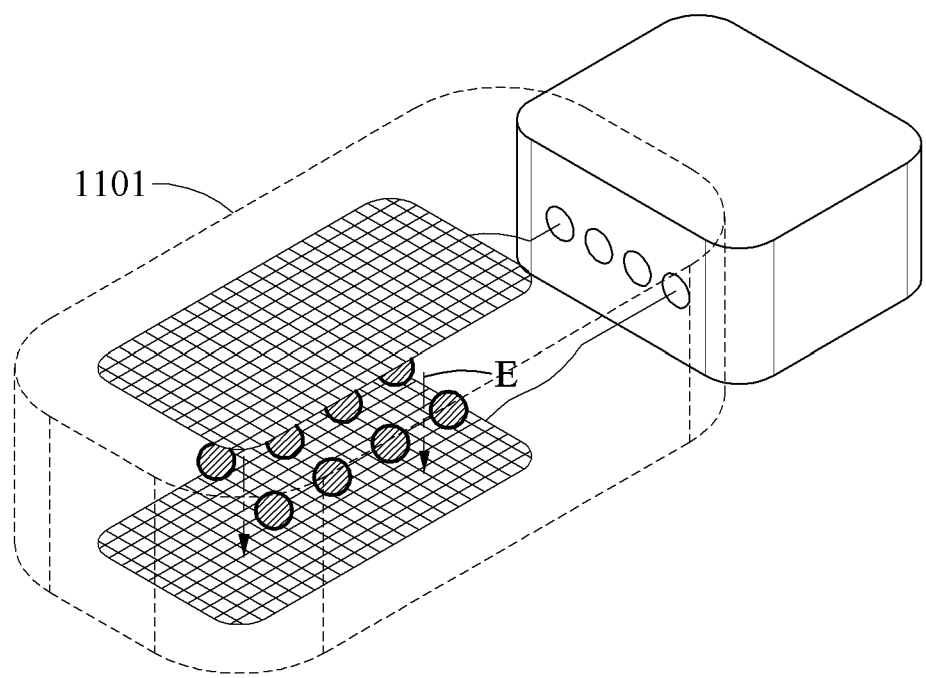
FIG. 11A illustrates an example of a structure of an object stimulation apparatus.
Figure 11B:
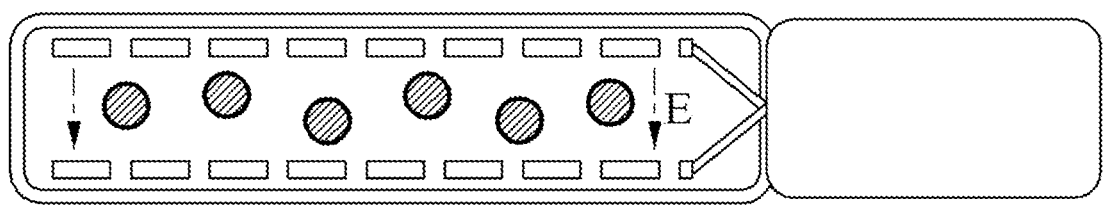
FIG. 11B illustrates an example of a cross-sectional diagram of an object stimulation apparatus in a vertical direction.
Figure 11C:
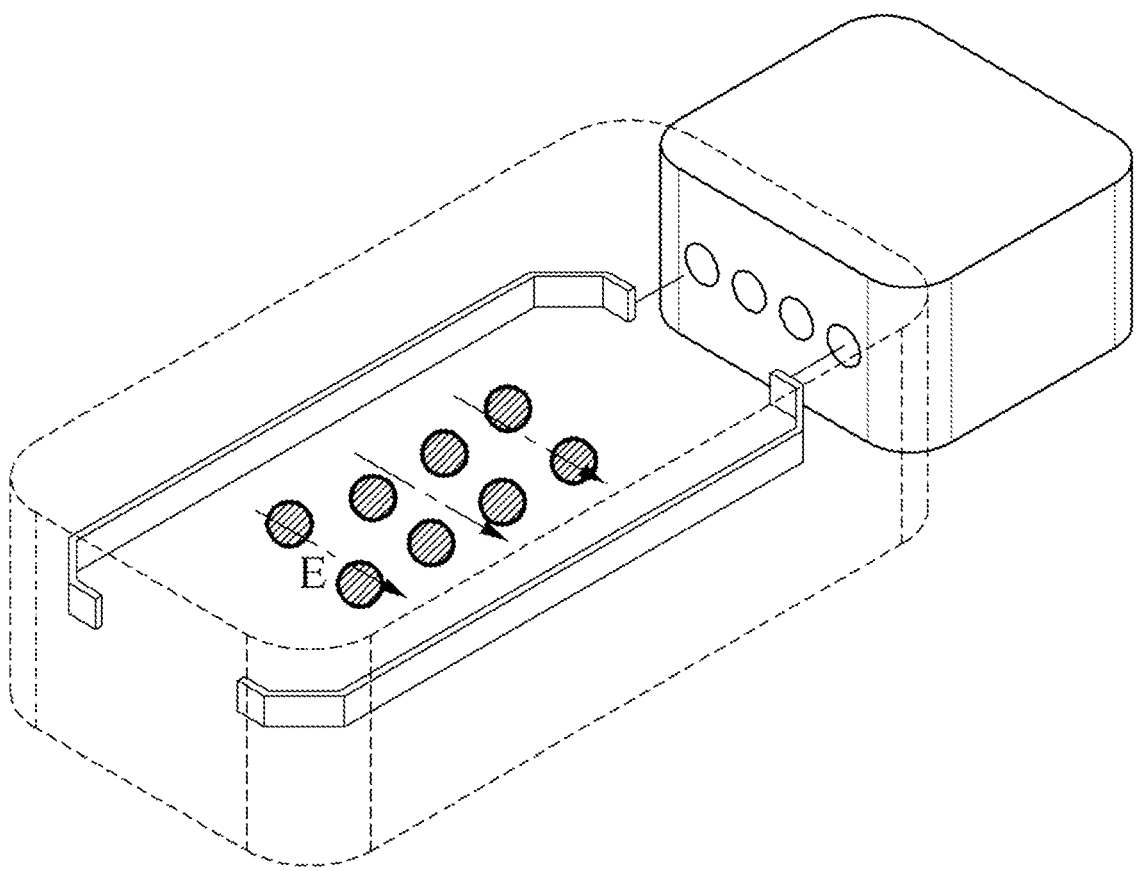
FIG. 11C illustrates an example of a structure of an object stimulation apparatus.
Figure 11D:
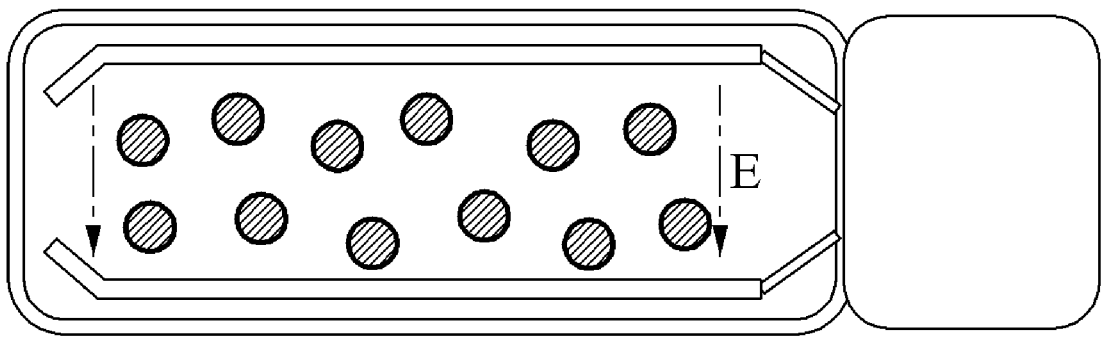
FIG. 11D illustrates an example of a cross-sectional diagram of an object stimulation apparatus in a horizontal direction.

FIG. 11A illustrates an example of a structure of an object stimulation apparatus. FIG. 11B illustrates an example of a cross-sectional diagram of an object stimulation apparatus (e.g., the object stimulation apparatus of FIG. 11A) in a vertical direction. FIG. 11C illustrates another example of a structure of an object stimulation apparatus. FIG. 11D illustrates an example of a cross-sectional diagram of an object stimulation apparatus (e.g., the object stimulation apparatus of FIG. 11C) in a horizontal direction.

The object stimulation apparatus may include a beta cell to protect the beta cell while promoting a function of the beta cell. To this end, the object stimulation apparatus may include a membrane 1101 and an electrode signal transceiver. The membrane 1101 may include a first electrode (e.g., the first electrode 111) and a second electrode (e.g., the second electrode 113).

The electrode signal transceiver may be connected to the first electrode and the second electrode. The electrode signal transceiver may apply an electrode signal to the beta cell through the first electrode and the second electrode. When the electrode signal is applied, the beta cell may perform a desired function. For example, an electrode may apply electrical stimulation to the beta cell, or may sense a concentration of glucose or an insulin secretion state.

The membrane 1101 may include the beta cell to protect and maintain the beta cell. To this end, the membrane 1101 may include a porous film. The porous film may include a plurality of pores having a diameter less than that of an immune cell and greater than that of a nutrient, to block an inflow of the immune cell and allow an inflow of the nutrient through the plurality of pores.

Referring to FIG. 11A, two electrodes with mesh structures may be included in the membrane 1101, and beta cells may be disposed between the two electrodes. An electrode signal transceiver may apply an electrode signal to a beta cell through an electrode. Referring to FIG. 11B, an electric field of an electrode signal applied to a beta cell may be formed in a vertical direction.

Referring to FIG. 11C, two electrodes with ribbon structures may be included in the membrane 1101, and beta cells may be disposed between the two electrodes. An electrode signal transceiver may apply an electrode signal to a beta cell through an electrode. Referring to FIG. 11D, an electric field of an electrode signal applied to a beta cell may be formed in a horizontal direction.

In addition, the object stimulation apparatus may receive wireless power. To this end, the object stimulation apparatus may further include an electrode capacitor connected between the first electrode and the second electrode, a power receiver connected to the first electrode and the second electrode, separately from the electrode signal transceiver, and a resonant capacitor configured to connect a conducting line between the first electrode and the power receiver and a conducting line between the second electrode and the power receiver. The first electrode and the second electrode may each have a shape of a coil, and may be wound in the same direction.

In response to a low-frequency signal, the electrode capacitor may be open and the electrode signal transceiver may apply an electrode signal to a beta cell. In response to a high-frequency signal, the electrode capacitor may be shorted so that the first electrode and the second electrode may form a single coil, and the power receiver may wirelessly receive power from a wireless power transmission apparatus to charge a battery.

The wireless power reception apparatuses, first electrodes, second electrodes, wireless power transmission apparatuses, electrode capacitors, electrode signal transceivers, power receivers, first inductors, second inductors, first capacitor and second capacitors, components, resonant capacitors, electrodes, ports, controllers, membranes, switches, wireless power reception apparatus 110, first electrode 111, second electrode 113, wireless power transmission apparatus 120, electrode capacitor 301, resonant capacitor 303, electrode signal transceiver 305, power receiver 307, first inductor and second inductor 311, first capacitor and second capacitor 313, component 701, resonant capacitor 703, electrode 1001, electrode 1003, electrode 1005, electrode 1007, port 1011, port 1013, port 1015, port 1017, switch SW, controller 719, membrane 1101, and other apparatuses, devices, units, modules, and components described herein with respect to FIGS. 1-11D are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-11D that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions used herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

What is claimed is:

1. A wireless power reception apparatus comprising:
a first electrode including a coil shape;
a second electrode including the coil shape;
an electrode capacitor connected between the first electrode and the second electrode;
an electrode signal transceiver connected to the first electrode and the second electrode;
a power receiver connected to the first electrode and the second electrode, separately from the electrode signal transceiver;
a resonant capacitor; and
a first capacitor and a second capacitor configured to selectively connect or disconnect a conducting line between the first electrode and the power receiver and a conducting line between the second electrode and the power receiver, depending on a selected frequency,
wherein the first electrode and the second electrode are wound in a same direction and are configured to form a single coil in response to the electrode capacitor being shorted.

2. The wireless power reception apparatus of claim 1, wherein the electrode signal transceiver is configured to apply a low-frequency signal to the first electrode and the second electrode such that the electrode capacitor and the first and second capacitors are open.

3. The wireless power reception apparatus of claim 2, wherein the first electrode and the second electrode are configured to apply an electrode signal to an object disposed between the first electrode and the second electrode, based on the low-frequency signal.

4. The wireless power reception apparatus of claim 1, wherein the first electrode and the second electrode are configured to receive a high-frequency signal from a wireless power transmission apparatus such that the electrode capacitor is shorted.

5. The wireless power reception apparatus of claim 4, wherein the first electrode and the second electrode are configured to form a single inductor, and the power receiver is charged with the high-frequency signal through a resonance by the single inductor and the resonant capacitor.

6. The wireless power reception apparatus of claim 4, wherein the first electrode and the second electrode are configured to receive the high-frequency signal from the wireless power transmission apparatus such that the first and second capacitors are shorted.

7. The wireless power reception apparatus of claim 1, wherein either one or both of the first electrode and the second electrode has a spiral structure.

8. The wireless power reception apparatus of claim 1, wherein either one or both of the first electrode and the second electrode has a mesh structure, and a conducting line between the mesh structure and the power receiver includes the coil shape enclosing the mesh structure.

9. The wireless power reception apparatus of claim 1, wherein either one or both of the first electrode and the second electrode includes a spiral-mesh structure.

10. The wireless power reception apparatus of claim 1, wherein
the first electrode and the second electrode are bracket-shaped conductors with a width, and
the first electrode and the second electrode form a circle.

11. The wireless power reception apparatus of claim 1, further comprising:
a first inductor connected between the first electrode and the electrode signal transceiver; and a second inductor connected between the second electrode and the electrode signal transceiver.

12. The wireless power reception apparatus of claim 1, further comprising:
a first switch connected between the first electrode and the electrode signal transceiver;
a second switch connected between the second electrode and the electrode signal transceiver; and
a controller configured to:
control the first switch and the second switch to be open in response to the first electrode and the second electrode receiving a high-frequency signal, and
control the first switch and the second switch to be shorted in response to a low-frequency signal being applied to the first electrode and the second electrode.

13. The wireless power reception apparatus of claim 1, wherein:
the first capacitor is connected between the first electrode and the power receiver; and
the second capacitor is connected between the second electrode and the power receiver.

14. The wireless power reception apparatus of claim 1, further comprising:
a housing comprising the electrode signal transceiver and the power receiver, wherein the electrode capacitor is entirely disposed outside the housing.

15. The wireless power reception apparatus of claim 1, wherein the first electrode and the second electrode are disposed on different sides of the wireless power reception apparatus, respectively.

16. The wireless power reception apparatus of claim 15, further comprising:
a housing comprising the electrode signal transceiver and the power receiver, wherein the electrode capacitor is entirely disposed outside the housing.

17. The wireless power reception apparatus of claim 1, further comprising:
a controller configured to control the resonant capacitor to increase a reception voltage by a high-frequency signal received from a wireless power transmission apparatus.

18. The wireless power reception apparatus of claim 1, further comprising:
a controller configured to generate a response signal in response to a test signal received from a wireless power transmission apparatus,
wherein the wireless power transmission apparatus is configured to determine whether impedance matching is performed based on the generated response signal, and
wherein the controller is configured to receive a control signal generated based on a result of the determining by the wireless power transmission apparatus and to control the resonant capacitor based on the control signal.

19. The wireless power reception apparatus of claim 1, wherein
whether impedance matching is performed is determined by a wireless power transmission apparatus based on a response signal generated in response to a test signal received from the wireless power transmission apparatus, and
the first electrode and the second electrode are configured to receive a resonant frequency signal selected based on a result of the determining by the wireless power transmission apparatus.

20. The wireless power reception apparatus of claim 1, wherein the electrode signal transceiver is configured to communicate with an external communicator using a low-frequency signal.

21. The wireless power reception apparatus of claim 1, wherein the selectively connecting to and disconnecting from the conducting line is performed in response to a signal with the selected frequency.

22. The wireless power reception apparatus of claim 1, wherein the resonant capacitor is configured to connect the conducting line between the first electrode and the power receiver and the conducting line between the second electrode and the power receiver.

23. The wireless power reception apparatus of claim 1, wherein the resonant capacitor includes at least one of a varactor and a cap bank, and is configured to be set with a capacitance to maximize a voltage of the first electrode or the second electrode.

24. An object stimulation apparatus comprising:
a membrane comprising a first electrode and a second electrode;
an electrode capacitor connected between the first electrode and the second electrode; and
an electrode signal transceiver selectively, based on an electrode signal with a selected frequency and upon receipt of the electrode signal, connected to or disconnected from the first electrode and the second electrode, and configured to apply the electrode signal to a beta cell through the first electrode and the second electrode,
wherein the first electrode and the second electrode are configured to form a single coil in response to the electrode capacitor being shorted.

* * * * *